(12) United States Patent
Hildebrand et al.

(10) Patent No.: US 8,431,772 B1
(45) Date of Patent: Apr. 30, 2013

(54) DIACYLGLYCEROL ACYLTRANSFERASE SEQUENCES AND RELATED METHODS

(75) Inventors: David Hildebrand, Lexington, KY (US); Runzhi Li, Lexington, KY (US); Tomoko Hatanaka, Kobe (JP)

(73) Assignee: University of Kentucky Research Foundation, Lexington, KY (US)

( * ) Notice: Subject to any disclaimer, the term of this patent is extended or adjusted under 35 U.S.C. 154(b) by 446 days.

(21) Appl. No.: 12/622,045

(22) Filed: Nov. 19, 2009

Related U.S. Application Data

(60) Provisional application No. 61/116,195, filed on Nov. 19, 2008, provisional application No. 61/149,896, filed on Feb. 4, 2009.

(51) Int. Cl.
| | |
|---|---|
| *A01H 1/00* | (2006.01) |
| *A01H 5/00* | (2006.01) |
| *A01H 5/10* | (2006.01) |
| *C12N 15/82* | (2006.01) |
| *C07H 21/04* | (2006.01) |
| *C07K 14/415* | (2006.01) |

(52) U.S. Cl.
USPC .......... 800/278; 800/281; 800/298; 536/23.2; 536/23.6; 435/410; 435/419; 435/468; 435/320.1

(58) Field of Classification Search .................. None
See application file for complete search history.

(56) References Cited

U.S. PATENT DOCUMENTS

| | | | |
|---|---|---|---|
| 6,329,518 B1 * | 12/2001 | Green et al. ................ | 536/23.6 |
| 6,552,250 B1 | 4/2003 | Nykiforuk et al. | |
| 6,791,008 B1 | 9/2004 | Banas et al. | |
| 6,822,141 B2 | 11/2004 | Lardizabal et al. | |
| 6,914,170 B2 | 7/2005 | Li et al. | |
| 6,995,301 B1 | 2/2006 | Shorrosh | |
| 7,015,373 B1 | 3/2006 | Zou et al. | |
| 7,067,718 B2 | 6/2006 | Anai et al. | |
| 7,135,617 B2 | 11/2006 | Lardizabal et al. | |
| 7,364,901 B2 | 4/2008 | Hildebrand et al. | |
| 7,417,176 B2 * | 8/2008 | Lardizabal et al. .......... | 800/281 |
| 2002/0078475 A1 | 6/2002 | Li et al. | |
| 2003/0028923 A1 | 2/2003 | Lardizabal et al. | |
| 2003/0074695 A1 | 4/2003 | Farese, Jr. et al. | |
| 2003/0115632 A1 | 6/2003 | Lardizabal et al. | |
| 2003/0167483 A1 | 9/2003 | Farese, Jr. et al. | |
| 2004/0073973 A1 | 4/2004 | Stymne et al. | |
| 2004/0078836 A1 | 4/2004 | Farese, Jr. et al. | |
| 2004/0107459 A1 | 6/2004 | Lardizabal et al. | |
| 2004/0111762 A1 | 6/2004 | Anai et al. | |
| 2004/0168213 A1 | 8/2004 | Verbsky et al. | |
| 2005/0005326 A1 | 1/2005 | Banas et al. | |
| 2005/0164192 A1 | 7/2005 | Graham et al. | |
| 2005/0170478 A1 | 8/2005 | Stymne et al. | |
| 2005/0172358 A1 | 8/2005 | Verbsky et al. | |
| 2005/0193446 A1 | 9/2005 | Zou et al. | |
| 2006/0064776 A1 | 3/2006 | Ruezinsky et al. | |
| 2006/0090222 A1 | 4/2006 | Zou et al. | |
| 2006/0094086 A1 | 5/2006 | Yadav et al. | |
| 2006/0094088 A1 | 5/2006 | Picataggio et al. | |
| 2006/0160193 A1 | 7/2006 | Yadav et al. | |
| 2006/0236425 A1 | 10/2006 | Shorrosh | |
| 2011/0218348 A1 * | 9/2011 | Zhou et al. .................... | 549/513 |

OTHER PUBLICATIONS

Ratliff et al, Abstract #P47012 from Poster Session at the American Society of Plant Biologist Meeting, Friday, Aug. 5-Wednesday Aug. 9, 2006 Boston Mass.*

Bafor M, Smith MA, Jonsson L, Stobart K and Stymme S (1993) Biosynthesis of vernoleate (cis-12-epoxyoctadecacis-9-enoate) in microsomal preparations from developing endosperm of *Euphorbia lagascae*. Archives of Biochemistry and Biophysics 303:145-151.

Burgal J, Shockey J, Lu C, Dyer J, Larson T, Graham I and Browse J (2008) Metabolic engineering of hydroxy fatty acid production in plants: RcDGAT2 drives dramatic increases in ricinoleate levels in seed oil. Plant Biotechnology Journal 8:819-831.

Cahoon EB, Shockey JM, Dietrich CR, Gidda SK, Mullen RT and Dyer JM (2007) Engineering oilseeds for sustainable production of industrial and nutritional feedstocks: solving bottlenecks in fatty acid flux. Current Opinion in Plant Biology 10:236-244.

Cahoon EB, Ripp KG, Hall SE and McGonigle B (2002) Transgenic production of epoxy fatty acids by expression of a cytochrome P450 enzyme from *Euphorbia lagascae* seed. Plant Physiology 128:615-624.

Cases S, Stone SJ, Zhou P, Yen E, Tow B, Lardizabal KD, Voelker T and Farese RV, Jr. (2001) Cloning of DGAT2, a Second Mammalian Diacylglycerol Acyltransferase, and Related Family Members. J Biol Chem 276:38870-38876.

Chen P-Y, Wang C-K, Soong S-C and to K-Y (2003) Complete sequence of the binary vector pB1121 and its application in cloning T-DNA insertion from transgenic plants. Molecular Breeding 11:287-293.

Lung S-C and Weselake R (2006) Diacylglycerol acyltransferase: a key mediator of plant triacylglycerol synthesis. Lipids 41:1073-1088.

Finer JJ and Nagasawa A (1988) Development of an embryogenic suspension culture of soybean (Glycine max Merrill.). Plant Cell Tissue and Organ Culture 15:125-136.

Hatanaka T, Shimizu R and Hildebrand D (2004) Expression of a Stokesia laevis epoxygenase gene. Phytochemistry 65:2189-2196.

(Continued)

*Primary Examiner* — Eileen B O Hara
(74) *Attorney, Agent, or Firm* — Stites & Harbison PLLC; Terry L. Wright

(57) ABSTRACT

Isolated nucleic acid and amino acid sequences encoding a diacylglycerol acyltransferase 2 (DGAT2) polypeptide are provided. Vectors and transgenic cells that include a nucleic acid sequence encoding a DGAT2 polypeptide are also described. Further provided are methods of producing an epoxy fatty acid by transforming a cell with a first isolated nucleic acid that encodes a diacylglycerol acyltransferase polypeptide and a second isolated nucleic acid that encodes an epoxygenase polypeptide, such that expression of the diacylglycerol acyltransferase polypeptide and the epoxygenase polypeptide increases an amount of epoxy fatty acid in the cell.

28 Claims, 8 Drawing Sheets

OTHER PUBLICATIONS

He X, Turner C, Chen G, Lin J-T and Mckeon T (2004) Cloning and characterization of a cDNA encoding diacylglycerol acyltransferase from castor bean. Lipids 39:311-318.

Jako C, Kumar A, Wei Y, Zou J, Barton DL, Giblin EM, Covello PS and Taylor DC (2001) Seed-Specific Over-Expression of an Arabidopsis cDNA Encoding a Diacylglycerol Acyltransferase Enhances Seed Oil Content and Seed Weight. Plant Physiol 126:861-874.

Jaworski J and Cahoon EB (2003) Industrial oils from transgenic plants. Current Opinin in plant Biology 6:178-184.

Kroon JTM, Wei W, Simon WJ and Slabas AR (2006) Identification and functional expression of a type 2 acyl-CoA: diacylglycerol acyltransferase (DGAT2) in developing castor bean seeds which has high homology to the major triglyceride biosynthetic enzyme of fungi and animals. Phytochemistry 67:2541-2549.

Lardizabal KD, Mai JT, Wagner NW, Wyrick A, Voelker T and Hawkins DJ (2001) DGAT2 is a new diacylglycerol acyltransferase gene family. Purification, cloning, and expression in insect sells of two polypeptides from Mortierella ramanniana with diacylglycerol acyltransferase activity. J Biol Chem 276:38862-38869.

Lee M, Lenman M, Banas A, Bafor M, Singh S, Schweizer M, Nilsson R, Liljenberg C, Dahlqvist A, Gummeson PO, Sjodahl S, Green A and Stymne S (1998) Identification of non-heme diiron proteins that catalyze triple bond and epoxy group formation. Science 280:915-918.

Lee S, Lee B, Jang I, Kim S and Bhak J (2006) Localizome: a server for identifying transmembrane topologies and TM helices of eukaryotic proteins utilizing domain information. Nud Acids Res 34:W99-W103.

Saha S, Enugutti B, Rajakumari S and Rajasekharan R (2006) Cytosolic Triacylglycerol Biosynthetic Pathway in Oilseeds. Molecular Cloning and Expression of Peanut Cytosolic Diacylglycerol Acyltransferase. Plant Physiology 141:1533-1543.

Samoylov VM, Tucker DM and Parrott WA (1998) a liquid medium-based protocol for rapid regeneration from embryogenic soybean cultures. Plant Cell Reports 18:49-54.

Schmidt M, Tucker D, Cahoon E and Parrott W (2005) Towards normalization of soybean somatic embryo maturation. Plant Cell Reports 24:383-391.

Shockey JM, Gidda SK, Chapital DC, Kuan J-C, Dhanoa PK, Bland JM, Rothstein SJ, Mullen RT and Dyer JM (2006) Tung Tree DGAT1 and DGAT2 Have Nonredundant Functions in Triacylglycerol Biosynthesis and Are Localized to Different Subdomains of the Endoplasmic Reticulum. Plant Cell 18:2294-2313.

Siloto, R.M.P., M. Truksa, D. Brownfield, A.G: Good, and R.J. Weselake. 2009. Directed evolution of acyl-CoA: diacylglycerol acyltransferase: Development and characterization of Brassica napus DGAT1 mutagenized libraries. Elsevier France-Editions Scientifiques Medicales Elsevier.

Siloto, R.M.P., M. Truksa, X.H. He, T. McKeon, and R.J. Weselake. 2009. Simple Methods to Detect Triacylglycerol Biosynthesis in a Yeast-Based Recombinant System. Lipids 44:963-973.

Singh SP, Zhou X-R, Liu Q, Stymne S and Green AG (2005) Metabolic engineering of new fatty acids in plants. Current Opinion in Plant Biology 8:197-203.

Singh S, Thomaeus S, Lee M, Stymne S and Green A (2001) Transgenic expression of a D12-epoxygenase gene in Arabidopsis seeds inhibits accumulation of linoleic acid. Planta 212:872-879.

Slightom JL, Sun SM and Hall TC (1983) Complete nucleotide sequence of a french bean storage protein gene: phaseolin. Proc Natl Acad Sci USA 80:1897-1901.

Spitzer V, Tomberg W and Zucolotto M (1996) Identification of $\alpha$-parinaric acid in the seed oil of Sebastiana . brasiliensis Sprengel (Euphorbiaceae). Journal of the American Oil Chemists' Society 73:569-573.

Stone SJ, Levin MC and Farese RV, Jr. (2006) Membrane Topology and Identification of Key Functional Amino Acid Residues of Murine Acyl-CoA:Diacylglycerol Acyltransferase-2. J Biol Chem 281:40273-40282.

Thelen JJ and Ohlrogge JB (2002) Metabolic engineering of fatty acid biosynthesis in plants. Metabolic Engineering 4:12-21.

Trick HN, Dinkins RD, Santarem ER, Di R, Samoylov VM, Meurer C, Walker D, Parrott WA, Finer JJ and Collins GB (1997) Recent advances in soybean transformation. Plant Tissue Culture and Biotechnology 3:9-26.

Vogel G and Browse J (1996) Choline phospho transferase and diacylglycerol acyl transferase:substrate specificities at a key branch point in seed lipid metabolism. Plant Physiology 110:923-931.

Wu S, Schoenbeck MA, Greenhagen4 BT, Takahashi S, Lee S, Coates RM and Chappell J (2005) Surrogate Splicing for Functional Analysis of Sesquiterpene Synthase Genes. Plant Physiology 138:1322-1333.

Xu, J.Y., T. Francis, E. Mietkiewska, E.M. Giblin, D.L. Barton, Y. Zhang, M. Zhang, and D.C. Taylor. 2008. Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content. Plant Biotechnology Journal 6:799-818.

Yu K, Li R, Hatanaka T and Hildebrand D (2008) Cloning and functional analysis of two type 1 diacylglycerol acyltransferases from Vernonia galamensis. Phytochemistry 69:1119-1127.

Yu K, McCracken CJ, Li R and Hildebrand DF (2006) Diacylglycerol acyltransferase from Vernonia and Stokesia prefer substrates with vernolic acid. Lipids 41:557-566.

Zhou X-R, Singh S, Liu Q and Green a (2006) Combined transgenic expression of $\Delta$12-desaturase and $\Delta$12-epoxygenase in high linoleic acid seeds leads to increased accumulation of vernolic acid. Functional Plant Biology 33:585-592.

Banas et al., "The involvement of phospholipid:diacylglycerol acyltransferases in triacylglycerol production," Biochem Soc Trans 28(6), 703-5 (Dec. 2000).

He et al., "Regulation of diacylglycerol acyltransferase in developing seeds of castor," Lipids 39(9), 865-71 (Sep. 2004).

He et al., "Diacylglycerol acyltransferase activity and triacylglycerol synthesis in germinating castor seed cotyledons," Lipids 41(3), 281-5 (Mar. 2006).

Milcamps et al., "Isolation of a gene encoding a 1,2-diacylglycerol-sn-acetyl-CoA acetyltransferase from developing seeds of Euonymus alatus," J Biol Chem 280(7), 5370-7 (Feb. 18, 2005) (Epub Dec. 3, 2004);.

Sorensen et al., "Storage lipid accumulation and acyltransferase action in developing flaxseed," Lipids 40(10), 1043-9 (Oct. 2005).

* cited by examiner

Diagram for seed-chipping

| Seed part | Mean Va % | SE |
|---|---|---|
| 1 | 25.7 | 0.4 |
| 2 | 24.7 | 0.6 |
| 3 | 25.4 | 0.5 |
| 4 | 24.3 | 0.6 |
| 5 | 26.6 | 0.4 |

DIACYLGLYCEROL ACYLTRANSFERASE SEQUENCES AND RELATED METHODS

RELATED APPLICATIONS

This application claims priority to U.S. Provisional Application Ser. No. 61/116,195, filed Nov. 19, 2008, and U.S. Provisional Application Ser. No. 61/149,896, filed Feb. 4, 2009, the entire disclosures of which are incorporated herein by this reference.

TECHNICAL FIELD

The presently-disclosed subject matter relates to diacylglycerol acyltransferase (DGAT) sequences and methods of using the same. In particular, the presently-disclosed subject matter relates to novel nucleic acid and amino acid sequences for DGAT and methods of using those sequences to increase the production of epoxy fatty acids.

BACKGROUND

Plant oil, largely in the form of triacylglycerol (TAG), is attractive as a renewable resource to supplant or replace petroleum as a source of many compounds. Unlike most commercial oilseeds containing oil comprised predominantly of just five main fatty acids, namely palmitic (C16:0), stearic (C18:0), oleic (C18:1), linoleic (C18:2) and α-linolenic (C18:3) acids, many exotic plant species have been found to contain high levels of unusual fatty acids, such as hydroxy, epoxy, and acetylenic fatty acids (van de Loo, et al., 1993). For example, an epoxy fatty acid, known as vernolic acid (cis-12-epoxyoctadeca-cis-9-enoic acid), can accumulate at levels up to 50-90% of the total fatty acids found in the seeds of *Vernonia galamensis, Euphorbia lagascae, Stokesia laevis, Crepis palaestina*, and *Bernardia pulchella* (Bafor, et al., 1993; Pascual and Correal, 1992; Perdue, 1989; Spitzer, et al., 1996; Thompson, et al., 1994). These unusual fatty acids have unique properties that make them valuable as renewable raw materials for the chemical industry, and, in fact, many of these unusual fatty acids are used in making dyes, paints, coatings, adhesives, composites, plastics, and a variety of other products (Jaworski and Cahoon, 2003). However, despite the value of these unusual fatty acids, the commercial production of the plants used to produce them has been significantly hampered due to the poor agronomic properties of those plants, such as low seed yields and low seed retention, which thus make the plants agronomically unsuited for industrial-scale growth and processing.

Metabolic engineering of oilseeds provides a platform for the production of these unusual fatty acids. However, recent efforts to express genes driving the synthesis of unusual fatty acids in commercial oil crops have been generally met with only limited success, with much lower amounts of the desired fatty acid accumulating in the oils of transgenic plants as compared with the native plant species (Burgal, et al., 2008; Cahoon, et al., 2007; Jaworski and Cahoon, 2003; Singh, et al., 2005; Thelen and Ohlrogge, 2002). Indeed, the transgenes used in these previous attempts to synthesize unusual fatty acids have been mainly divergent members of the Δ12-oleic acid desaturase gene family, which encode alternative enzymatic functions, such as epoxidation, hydroxylation, acetylenation, and conjugation, rather than the function of the typical fatty acid desaturase that catalyzes the introduction of a cis-Δ12 double bond in oleic acid (C18:1) to form linoleic acid (C18:2). As such, it is clear from these previous reports that for developing engineered oilseeds that accumulate higher levels of industrially-important unusual fatty acids, additional genes are needed, including genes responsible for the efficient and selective flux of unusual fatty acids from the site of synthesis on phospho lipids to storage in TAGs.

SUMMARY

This summary describes several embodiments of the presently-disclosed subject matter, and, in many cases, lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes diacylglycerol acyltransferase (DGAT) nucleic acid and amino acid sequences, as well as methods of using those sequences to increase the production of epoxy fatty acids.

In some embodiments of the presently-disclosed subject matter, an isolated nucleic acid sequence is provided that comprises a sequence of SEQ ID NO: 1. In some embodiments, an isolated nucleic acid sequence is provided that encodes a polypeptide comprising an amino acid sequence of SEQ ID NO: 2. In some embodiments, the nucleic acid encodes a diacylglycerol acyltransferase 2 (DGAT2) polypeptide. In some embodiments, the isolated nucleic acid sequences of the presently-disclosed subject matter further comprise a sequence that selectively hybridizes to the sequence of SEQ ID NO: 1 and, in some embodiments, that sequence is complementary to the sequence of SEQ ID NO: 1.

In some embodiments of the presently-disclosed subject matter, an isolated polypeptide is provided that comprises the sequence of SEQ ID NO: 2 or a sequence that is about 85% homologous to the sequence of SEQ ID NO: 2. In some embodiments, the polypeptide is encoded by a nucleic acid sequence comprising the sequence of SEQ ID NO: 1. In other embodiments, the polypeptide is encoded by a nucleic acid sequence that is complementary to a nucleic acid sequence that selectively hybridizes to the sequence of SEQ ID NO: 1. In some embodiments, the polypeptide is a DGAT2 polypeptide Further provided, in some embodiments, are vectors that include a nucleic acid sequence of the presently-disclosed subject matter. In some embodiments, a vector is provided that comprises an isolated nucleic acid encoding polypeptide comprising an amino acid sequence of SEQ ID NO: 2. In some embodiments, a vector is provided where the isolated nucleic acid is operably linked to an expression cassette, which, in some embodiments, includes a seed-specific promoter or a constitutive promoter.

In some embodiments of the presently-disclosed subject matter, transgenic plant cells are provided. In some embodiments, a transgenic plant cell is provided that comprises a vector that includes an isolated nucleic acid sequence that encodes a polypeptide comprising an amino acid sequence of SEQ ID NO: 2. In some embodiments, the transgenic plant cell comprises an isolated nucleic acid that is operably linked to an expression cassette, which, in some embodiments, can further include a seed-specific or a constitutive promoter.

Still further provided, in some embodiments of the presently-disclosed subject matter, are methods for producing an epoxy fatty acid. In some embodiments, a method of producing an epoxy fatty acid is provided that comprises transforming a cell with a first isolated nucleic acid that encodes a diacylglycerol acyltransferase (DGAT) polypeptide and a second isolated nucleic acid that encodes an epoxygenase (EPX) polypeptide such that expression of the DGAT polypeptide and the EPX polypeptide increases an amount of epoxy fatty acid in the cell. In some embodiments, transforming the cell with the first isolated nucleic acid and the second isolated nucleic acid comprises transforming the cell with a vector that includes the first isolated nucleic acid and a vector that includes the second isolated nucleic acid. In some embodiments, the first isolated nucleic acid and the second isolated nucleic acid are each operatively linked to an expression cassette, which, in some embodiments, includes a seed-specific promoter or a constitutive promoter.

In some embodiments of the presently-disclosed methods of producing an epoxy fatty acid, the DGAT polypeptide is a diacylglycerol acyltransferase 1 (DGAT1) polypeptide. In some embodiments, the DGAT1 polypeptide is a diacylglycerol acyltransferase 1a (DGAT1a) polypeptide, such as a DGAT1a polypeptide that is encoded by the nucleic acid sequence of SEQ ID NO: 4. In some embodiments, the DGAT1 polypeptide is a diacylglycerol acyltransferase 1b (DGAT1b) polypeptide, such as a DGAT1b polypeptide that is encoded by the nucleic acid sequence of SEQ ID NO: 17. In other embodiments, the DGAT polypeptide is a DGAT2 polypeptide, such as the DGAT2 polypeptide that is encoded by the nucleic acid sequence of SEQ ID NO: 1. In some embodiments, the epoxygenase polypeptide used in the presently-disclosed methods of producing an epoxy fatty acid is encoded by a nucleic acid sequence of SEQ ID NO: 5.

In some embodiments of the presently-disclosed methods of producing an epoxy fatty acid, the epoxy fatty acid is vernolic acid. In some embodiments, the amount of vernolic acid produced in a cell by the presently-disclosed methods is about 14 percent to about 26 percent.

Advantages of the presently-disclosed subject matter will become evident to those of ordinary skill in the art after a study of the description, Figures, and non-limiting Examples in this document.

BRIEF DESCRIPTION OF THE DRAWINGS

FIG. 1A is a schematic diagram showing the alignment of DGAT2 polypeptides from five different plant species including VgDGAT2 (SEQ ID NO: 2); RcDGAT2 (SEQ ID NO: 13); VfDGAT2 (SEQ ID NO: 14); AtDGAT2 (SEQ ID NO: 15); and OsDGAT2 (SEQ ID NO: 16) polypeptides, where amino acids identical in all five polypeptides are shaded in black, two predicted membrane spanning domains are underlined, and a C-terminal endoplasmic reticulum (ER) retrieval motif is boxed. FIG. 1B is a schematic diagram showing a phylogenetic analysis of various DGAT2 polypeptide sequences from plants, yeast, and animals, where the units at the bottom of the neighbor joining tree indicate the number of substitution events and where a *Vernonia galamensis* diacylglycerol acyltransferase 1b polypeptide (VgDGAT1) (GENBANK® Accession No. EF653277) was used as the outgroup for comparison.

BRIEF DESCRIPTION OF THE SEQUENCE LISTING

Figure 1A:
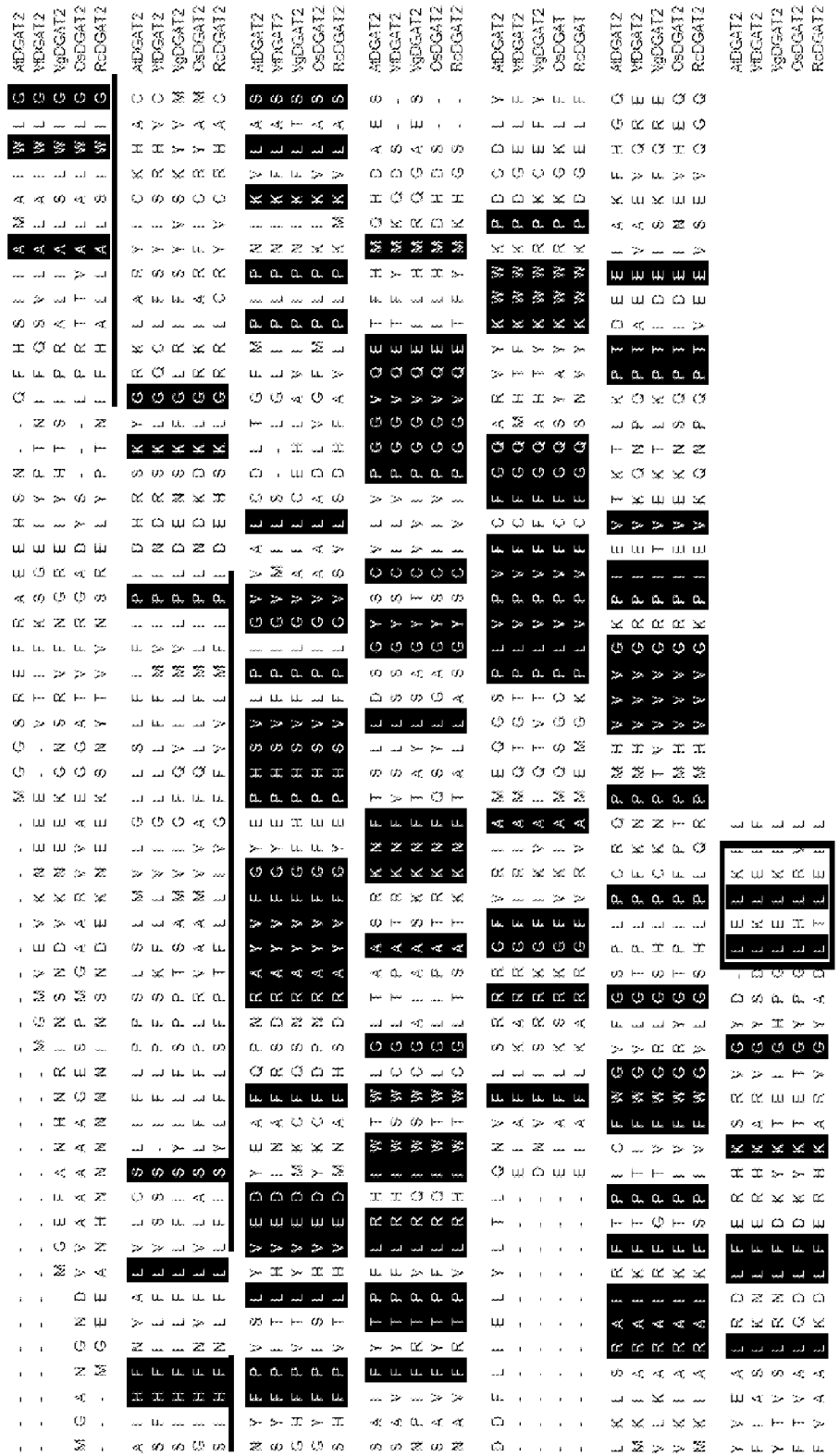
FIGS. 1A and 1B include schematic diagrams showing sequence analyses of the amino acid sequence of a diacylglycerol acyltransferase 2 (DGAT2) polypeptide from *Vernonia galamensis* (VgDGAT2: GENBANK® Accession No. FJ652577) in comparison with other DGAT2 polypeptides, including those from: *Caenorhabditis elegans* (CeDGAT2A: GENBANK® Accession No. Z81557; CeDGAT2B: GENBANK® Accession No. U64852); *Mus musculus* (MmDGAT2: GENBANK® Accession No. AK002443); *Mortierella ramanniana* (MrDGAT2A: GENBANK® Accession No. AF391089; MrDGAT2B: GENBANK® Accession No. AF391090); *Saccharomyces cerevisiae* (ScDGAT2: GENBANK® Accession No. NC001147); *Arabidopsis thaliana* (AtDGAT2: GENBANK® Accession No. NM115011.3); *Vernicia fordii* (tung tree) (VfDGAT2: GENBANK® Accession No. ABC94473); *Ricinus communis* (castor) (RcDGAT2: GENBANK® Accession No. AY916129); *Triticum aestivum* (wheat) (TaDGAT2: GENBANK® Accession No. TC208469); *Oryza sativa* (rice) (OsDGAT2: GENBANK® Accession No. NP1057530.1); and *Brassica napus* (canola or rapeseed) (BnDGAT2: GENBANK® Accession No. AF155224).

SEQ ID NO: 1 is a nucleic acid sequence of the open reading frame (ORF) of a diacylglycerol acyltransferase 2 (DGAT2) gene from *Vernonia galamensis*.

SEQ ID NO: 2 is an amino acid sequence of a DGAT2 polypeptide from *Vernonia galamensis*.

SEQ ID NO: 3 is a nucleic acid sequence of a full-length DGAT2 gene from *Vernonia galamensis*.

SEQ ID NO: 4 is a nucleic acid sequence of a diacylglycerol acyltransferase 1a (DGAT1a) cDNA obtained from *Vernonia galamensis*.

SEQ ID NO: 5 is a nucleic acid sequence of an epoxygenase cDNA obtained from *Stokesia laevis*.

SEQ ID NO: 6 is an amino acid sequence of an endoplasmic reticulum (ER) retrieval motif of a *Vernonia galamensis* DGAT2 protein.

SEQ ID NO: 7 is a nucleic acid sequence of a forward primer for amplifying *Vernonia galamensis* DGAT1a cDNA.

SEQ ID NO: 8 is a nucleic acid sequence of a reverse primer for amplifying *Vernonia galamensis* DGAT1a cDNA.

SEQ ID NO: 9 is a nucleic acid sequence of a forward primer for amplifying *Vernonia galamensis* DGAT2 cDNA.

SEQ ID NO: 10 is a nucleic acid sequence of a reverse primer for amplifying *Vernonia galamensis* DGAT2 cDNA.

SEQ ID NO: 11 is a nucleic acid sequence of a forward primer for amplifying a portion of an actin gene.

SEQ ID NO: 12 is a nucleic acid sequence of a reverse primer for amplifying a portion of an actin gene.

SEQ ID NO: 13 is an amino acid sequence of a DGAT2 polypeptide from *Ricinus communis* (castor).

SEQ ID NO: 14 is an amino acid sequence of a DGAT2 polypeptide from *Vernicia fordii* (tung tree).

SEQ ID NO: 15 is an amino acid sequence of a DGAT2 polypeptide from *Arabidopsis thaliana*.

SEQ ID NO: 16 is an amino acid sequence of a DGAT2 polypeptide from *Oryza satvia* (rice).

SEQ ID NO: 17 is a nucleic acid sequence of a diacylglycerol acyltransferase 1b (DGAT1b) cDNA obtained from *Vernonia galamensis*.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the terms used herein are believed to be well-understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

The production of seed oils in plants typically involves de novo fatty acid synthesis in plastids, fatty acid modification by membrane-bound enzymes in the endoplasmic reticulum (ER), fatty acid incorporation into triacylglycerol (TAG), and subsequent accumulation in oil bodies that bud off from the ER. In this regard, unusual fatty acids, such as hydroxyl, epoxy, and acetylenic fatty acids, are often first formed on phosphatidylcholine (PC) in the ER though the modification of oleic (C18:1) or linoleic (C18:2) acids by fatty acid desaturase 2 (FAD2)-like enzymes or by cytochrome P-450s. Regardless of the particular synthesis mechanism for the fatty acid, however, in the ER, the sequential incorporation of fatty acids onto TAG is commonly known as the Kennedy pathway, which consists of three successive acylation reactions of the hydroxyl groups of glycerol by three acyl-CoA-dependent acyltransferases, starting from glycerol-3-phosphate (G3P). Specifically, in the Kennedy pathway, lysophosphatidic acid (LPA) and phosphatidic acid (PA) are first formed through two acylations catalyzed by the acyltransferases glycerol-3-phosphate (GPAT) and lyso-phosphatidic acid acyltransferase (LPAAT). PA is then dephosphorylated by the action of phosphatidate phosphatase (PAP) to form sn-1,2-diacylglycerol(sn-1,2 DAG). The final acylation of sn-1,2 DAG is the transfer of a fatty acyl moiety, such as from acyl-CoA, to the sn-3 position of diacylglycerol by diacylglycerol acyltransferase (DGAT) to generate TAG.

It is thought that DGAT is one of the rate-limiting steps in plant storage lipid accumulation and plays a role in controlling both the quantitative and qualitative flux of fatty acids into storage TAGs. There are two distinct types of non-homologous DGAT gene families designated as DGAT1 and DGAT2 encoding proteins with DGAT activity in plants (Lardizabal, et al. 2001; Shockey, et al. 2006) and animals (Cases, et al. 2001). Furthermore, in certain species, such as soybean, *Vernonia galamensis*, and *Euphorbia* species, DGAT1 genes can further be divided into two distinct sub-classes, designated DGAT1a and DGAT1b. Recently, the specific functions of both DGAT1 and DGAT2 in the high accumulation of unusual fatty acids, such as epoxy and hydroxy fatty acids, in seed oils are beginning to be determined (see, e.g., He, et al. 2004; Kroon, et al. 2006; Shocky, et al. 2006; Burgal, et al. 2008).

For industrial applications, however, epoxy fatty acids are still currently produced by chemical epoxygenation of the carbon double bonds present in highly unsaturated vegetable oils, such as soybean and linseed oils, or by synthesis from petrochemicals. As such, it would be desirable, both from an economic and environmental standpoint, to transfer the synthesis pathway of epoxy fatty acids from the wild plant species into oil crops by metabolic engineering, as many of the wild plant species are not suited for the industrial scale growth and processing that is commonly seen in many oil seed crops.

Disclosed herein are data demonstrating that DGAT nucleic acid and amino acids sequences can be used to affect a change in the accumulation of epoxy fatty acids in cells. As disclosed herein, DGAT proteins were expressed in cells of various plant species in combination with an epoxygenase protein, and it was ascertained that the co-expression of these proteins resulted in an increase of total epoxy fatty acid levels, including levels of vernolic acid, in these cells. To that end, the presently-disclosed subject matter includes isolated DGAT nucleotide and amino acid sequences, as well as methods of using these sequences to increase the amounts of epoxy fatty acids in cells.

In some embodiments of the presently-disclosed subject matter, isolated nucleic acids are provided. In some embodiments, an isolated nucleic acid is provided that comprises a sequence of SEQ ID NO: 1. In some embodiments, an isolated nucleic acid is provided that is isolated from *Vernonia galamensis*. In some embodiments, an isolated nucleic acid is provided that is isolated from a DGAT2 gene that encodes a *Vernonia galamensis* DGAT2 polypeptide.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "nucleic acid" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated," when used in the context of an isolated nucleic acid or an isolated polypeptide, is a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The term "degenerate variant" refers to a nucleic acid having a residue sequence that differs from a reference nucleic acid by one or more degenerate codon substitutions. Degenerate codon substitutions can be achieved by generating sequences in which the third position of one or more selected (or all) codons is substituted with mixed base and/or deoxyinosine residues (Batzer, et al. 1991; Ohtsuka, et al. 1985; Rossolini, et al. 1994).

In some embodiments, an isolated nucleic acid sequence is provided that selectively hybridizes to the sequence of SEQ ID NO: 1. The term "selectively hybridize" as used herein refers to the ability of a nucleic acid sequence to hybridize to a target polynucleotide (e.g., a polynucleotide of SEQ ID NO: 1) with specificity. Thus, the nucleic acid sequence comprises a polynucleotide sequence that is complementary, or essentially complementary, to at least a portion of the target polynucleotide sequence. For example, in some embodiments, the nucleic acid sequence that selectively hybridizes to the sequence of SEQ ID NO: 1 is complementary to the sequence of SEQ ID NO: 1. Nucleic acid sequences which are "complementary" are those which are base-pairing according to the standard Watson-Crick complementarity rules. As used herein, the term "complementary sequences" means nucleic acid sequences which are substantially complementary, as can be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide. With regard to the nucleic acid sequences disclosed herein as selectively hybridizing to the sequence of SEQ ID NO: 1, the hybridizing nucleic acid sequence need not necessarily be completely complementary to the nucleic acid of SEQ ID NO: 1 along the entire length of the target polynucleotide so long as the hybridizing nucleic acid sequence can bind the nucleic acid of SEQ ID NO: 1 with specificity. In some embodiments, the nucleic acid sequences that selectively hybridize to the sequence of SEQ ID NO: 1 are about 80%, about 85%, about 90%, about 95%, about 98%, or about 100% complementary to the sequence of SEQ ID NO: 1.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. For example, in some embodiments, nucleic acid hybridization can be performed at 60° C. with 0.1× sodium citrate-sodium chloride (SSC) and 0.1% sodium dodecyl sulfate (SDS). However, the combination of parameters is much more important than the measure of any single parameter. (See, e.g., Wetmur & Davidson, 1968). Determining appropriate hybridization conditions to identify and/or isolate sequences containing high levels of homology is well known in the art. (See, e.g., Sambrook, et al., 1989).

In some embodiments of the presently-disclosed subject matter, an isolated nucleic acid is provided that encodes a polypeptide comprising an amino acid sequence of SEQ ID NO: 2. In some embodiments, an isolated nucleic acid sequence is provided that encodes a DGAT2 polypeptide, such as a DGAT2 polypeptide isolated from *Vernonia galamensis*.

The terms "polypeptide," "protein," and "peptide," which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment," when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

A fragment can also be a "functional fragment," in which case the fragment retains some or all of the activity of the reference polypeptide as described herein. For example, in some embodiments, a functional fragment of a DGAT2 polypeptide can retain some or all of the ability of the reference polypeptide to catalyze the final acylation step during TAG synthesis, such as what had been described for DGAT1 polypeptides (see, e.g., Siloto, et al., 2009; Siloto, et al., 2009; and Xu, et al. 2008).

The terms "modified amino acid," "modified polypeptide," and "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, a functional variant of a DGAT2 polypeptide retains some or all of the ability of the reference polypeptide to catalyze the final acylation step during TAG synthesis.

The term functional variant also includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitutions, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically-derivatized residue, provided that the resulting peptide maintains some or all of the activity of the reference peptide as described herein.

Further provided in some embodiments of the presently-disclosed subject matter are isolated polypeptides. In some embodiments, an isolated polypeptide is provided that comprises a sequence of SEQ ID NO: 2 or a sequence that is about 85% homologous to SEQ ID NO: 2. The terms "homologous," "homology," or "percent homology" when used herein to describe an amino acid sequence or a nucleic acid sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). Percent homology of sequences can be determined using the most recent version of BLAST, as of the filing date of this application.

In some embodiments, an isolated polypeptide is provided that is encoded by a nucleic acid sequence comprising the sequence of SEQ ID NO: 1. In some embodiments, the isolated polypeptide is encoded by a nucleic acid sequence that is complementary to a nucleic acid sequence that selectively hybridizes to the sequence of SEQ ID NO: 1. In some embodiments, the polypeptide is a DGAT2 polypeptide, such as a *Vernonia galamensis* DGAT2 polypeptide.

*Vernonia galamensis* is a plant in the sunflower family of significant industrial value due to high levels of vernolic acid, an epoxy fatty acid, found within the seeds of the plant. Indeed, *Vernonia galamensis* is commonly grown as a source of vernolic acid, which is then used in a variety of industrial applications, such as the manufacture of plastics or paints. However, the large-scale farming of *Vernonia galamensis* is typically not economically feasible, particularly outside of equatorial regions, due to poor seed yield and poor seed retention, which thus makes the plants agronomically unsuited for the industrial scale growth and processing that would be required to make use of *Vernonia galamensis* plants as a viable source of epoxy fatty acids. Disclosed herein, however, are data indicating the DGAT genes from *Vernonia galamensis*, such as *Vernonia galamensis* DGAT2 genes, can be inserted into a vector and then efficiently and economically used to produce DGAT polypeptides that, in combination with an epoxygenase polypeptide, are capable of increasing the production of epoxy fatty acids in plants that can be grown on a commercial scale.

In some embodiments of the presently-disclosed subject matter, vectors that include one or more of the isolated nucleic acid sequences disclosed herein are provided. In some embodiments, a vector is provided that includes an isolated nucleic acid comprising a sequence of SEQ ID NO: 1. In some embodiments, a vector is provided that includes an isolated nucleic acid sequence that encodes a polypeptide comprising an amino acid sequence of SEQ ID NO: 2.

The term "vector" is used herein to refer to any vehicle that is capable of transferring a nucleic acid sequence into another cell. For example, vectors which may be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art. In some embodiments, the vectors of the presently-disclosed subject matter are plasmids, such as the plasmid pBI121 or the pCAMBIA1301 plasmid.

In some embodiments, the isolated nucleic acid included in the vector is operably linked to an expression cassette. The terms "associated with," "operably linked," and "operatively linked" refer to two nucleic acid sequences that are related physically or functionally. For example, a promoter or regulatory DNA sequence is said to be "associated with" a DNA sequence that encodes an RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

In some embodiments, an expression cassette is provided that comprises a "constitutive promoter," such as a 35S promoter, a figwort mosaic promoter, or the constitutive plant promoter of ubiquitin, that continually expresses a nucleic acid sequence of the presently-disclosed subject matter in all types of cells where it is inserted. For some applications, it is useful to direct the expression of a nucleic acid sequence of the presently-disclosed subject matter to different tissues of a plant. As such, in some embodiments, an expression cassette is provided that comprises a "seed-specific promoter," such as a phaseolin, glycinin, conglycinin, seed lectin, napin, cruferin, or other seed-specific promoter that expresses a nucleic acid sequence of the presently-disclosed subject matter only in seeds of a desired plant.

The presently-disclosed subject matter also provides transgenic plant cells or plants that have been transformed with one or more of the vectors disclosed herein. As used herein, the term "plant cell" is understood to mean any cell derived from a monocotyledonous or a dicotyledonous plant and capable of constituting undifferentiated tissues such as calli, differentiated tissues such as embryos, portions of monocotyledonous plants, monocotyledonous plants or seed. The term "plant" is understood to mean any differentiated multi-cellular organism capable of photosynthesis, including monocotyledons and dicotyledons. In some embodiments, the plant cell can be an *Arabidopsis* plant cell, a tobacco plant cell, a soybean plant cell, a petunia plant cell, or a cell from another oilseed crop including, but not limited to, a canola plant cell, a rapeseed plant cell, a palm plant cell, a sunflower plant cell, a cotton plant cell, a corn plant cell, a peanut plant cell, a flax plant cell, and a sesame plant cell.

The terms "transformed," "transgenic," and "recombinant" are used herein to refer to a cell of a host organism, such as a plant, into which a heterologous nucleic acid molecule has been introduced. The nucleic acid molecule can be stably integrated into the genome of the cell or the nucleic acid molecule can also be present as an extrachromosomal molecule. Such an extrachromosomal molecule can be auto-replicating. Transformed cells, tissues, or subjects are understood to encompass not only the end product of a transformation process, but also transgenic progeny thereof.

The terms "heterologous," "recombinant," and "exogenous," when used herein to refer to a nucleic acid sequence (e.g., a DNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found. Similarly, when used in the context of a polypeptide or amino acid sequence, an exogenous polypeptide or amino acid sequence is a polypeptide or amino acid sequence that originates from a source foreign to the particular host cell or, if from the same source, is modified from its original form. Thus, exogenous DNA segments can be expressed to yield exogenous polypeptides.

Introduction of a nucleic acid (e.g., a nucleic acid incorporated into an appropriate vector) of the presently-disclosed subject matter into a plant cell can be performed by a variety of methods known to those of ordinary skill in the art including, but not limited to, insertion of a nucleic acid sequence of interest into an *Agrobacterium rhizogenes* Ri or *Agrobacterium tumefaciens* Ti plasmid, microinjection, electroporation, or direct precipitation. By way of providing an example, in some embodiments, transient expression of a nucleic acid sequence or gene of interest can be performed by agro-infiltration methods. In this regard, a suspension of *Agrobacterium tumefaciens* containing a nucleic acid sequence or gene of interest can be grown in culture and then injected into a plant by placing the tip of a syringe against the underside of a leaf while gentle counter-pressure is applied to the other side of the leaf The *Agrobacterium* solution is then injected into the airspaces inside the leaf through stomata. Once inside the leaf, the *Agrobacterium* transforms the gene of interest to a portion of the plant cells where the gene is then transiently expressed.

As another example, transformation of a plasmid or nucleic acid of interest into a plant cell can be performed by particle gun bombardment techniques. In this regard, a suspension of plant embryos can be grown in liquid culture and then bombarded with plasmids or nucleic acids that are attached to gold particles, wherein the gold particles bound to the plasmid or nucleic acid of interest can be propelled through the membranes of the plant tissues, such as embryonic tissue. Following bombardment, the transformed embryos can then be selected using an appropriate antibiotic to generate new, clonally propagated, transformed embryogenic suspension cultures.

For additional guidance regarding methods of transforming and producing transgenic plant cells, see U.S. Pat. Nos. 4,459,355; 4,536,475; 5,464,763; 5,177,010; 5,187,073; 4,945,050; 5,036,006; 5,100,792; 5,371,014; 5,478,744; 5,179,022; 5,565,346; 5,484,956; 5,508,468; 5,538,877; 5,554,798; 5,489,520; 5,510,318; 5,204,253; 5,405,765; EP Nos. 267,159; 604,662; 672,752; 442,174; 486,233; 486,234; 539,563; 674,725; and, International Patent Application Publication Nos. WO 91/02071 and WO 95/06128, each of which is incorporated herein by this reference.

Still further provided, in some embodiments of the presently-disclosed subject matter, are methods of producing an epoxy fatty acid. The term "epoxy fatty acids" is used herein to refer to an acyl chain of a fatty acid that contains an epoxide bridge (i.e., an oxygen atom covalently bound to carbon atoms that are in turn covalently bound to each other to form a three-member ring that is part of a larger molecular structure). In plants, the biochemical reaction responsible for the production of epoxy fatty acid is often catalyzed by an epoxygenase enzyme, which is capable of combining common fatty acids with oxygen to form epoxy fatty acids (see, e.g., U.S.

Pat. No. 7,364,901, which is incorporated herein by this reference). For example, an epoxygenase catalyzes the conversion of linoleic acid into the epoxy fatty acid vernolic acid (cis-12-epoxyoctadeca-cis-9-enoic acid). It has been determined, however, that by co-expressing a nucleic acid encoding an epoxygenase polypeptide with a nucleic acid encoding a DGAT polypeptide in plant cells, the levels of epoxy fatty acids, such as vernolic acid, can be significantly increased in the plant cells as compared to wild-type plant cells or plant cells expressing DGAT genes or epoxygenase genes by themselves In some embodiments of the presently-disclosed methods, a method of producing an epoxy fatty acid is provided that comprises transforming a cell with a first nucleic acid that encodes a DGAT polypeptide and a second isolated nucleic acid that encodes an epoxygenase polypeptide such that the expression of the DGAT polypeptide and the epoxygenase polypeptide increases an amount of epoxy fatty acid in the cell. In some embodiments of the presently-disclosed subject matter, the epoxy fatty acid is vernolic acid The "amount" of an epoxy fatty acid in a cell can be determined by methods known to those of ordinary skill in the art. For example, gas chromatography-mass spectrometry, thin layer chromatography-gas chromatography, or gas chromatography can be utilized to determine a total amount of epoxy fatty acids or an amount of a particular epoxy fatty acid, such as vernolic acid, in a sample obtained from a cell transformed with a nucleic acid of the presently-disclosed subject matter. An increase in the amount of an epoxy fatty acid can then be measured relative to a control level of the epoxy fatty acid, such as an amount or range of amounts of the epoxy fatty acid found in a comparable samples in cells that have not been transformed with a nucleic acid of the presently-disclosed subject matter. In some embodiments, the increase in the amounts of an epoxy fatty acid can be about 1%, about 5%, about 10%, about 15%, about 20%, about 25%, about 30%, about 40%, about 45%, or about 50%. In some embodiments, the increase in the amounts of an epoxy fatty acid is about 14% to about 26%.

In some embodiments of the methods for producing an epoxy fatty acid, transforming the cell with the first isolated nucleic acid and the second isolated nucleic acid comprises transforming the cell with a vector that includes the first isolated nucleic acid and a vector that includes the second isolated nucleic acid. For example, in some embodiments, a nucleic acid encoding a DGAT polypeptide can be inserted into an appropriate vector as described herein and a nucleic acid encoding an epoxygenase polypeptide can be inserted into another vector. In some embodiments, each of the vectors can then be electroporated into *Agrobacterium tumefacians* cells, which can then be used to transform cells with the vectors according to agro-infiltration methods known to those of ordinary skill in the art.

In some embodiments of the presently-disclosed methods for producing an epoxy fatty acid, which make use of vectors that include nucleic acids of interest, the first isolated nucleic acid and second isolated nucleic acid are each operatively linked to an expression cassette. In some embodiments, each expression cassette includes a seed-specific promoter or a constitutive promoter such that the expression of the nucleic acids can be directed to seed cells or can be directed to express in all cell types of a host, to the extent it may be desired.

In some embodiments of the presently-disclosed methods, the DGAT polypeptide that is expressed in a cell is a DGAT1 polypeptide. In some embodiments, the DGAT1 polypeptide is a DGAT1a polypeptide, such as a *Vernonia galamensis* DGAT1a polypeptide (see, e.g., GENBANK® Accession No. EF653276.1, which is incorporated herein by this reference). In some embodiments, the DGAT1a polypeptide is encoded by a nucleic acid sequence of SEQ ID NO: 4. In some embodiments, the DGAT1 polypeptide is a DGAT1b polypeptide, such as a *Vernonia galamensis* DGAT1b polypeptide (see, e.g., GENBANK® Accession No. EF653277, which is incorporated herein by this reference). In some embodiments, the DGAT1b polypeptide is encoded by a nucleic acid sequence of SEQ ID NO: 17.

In other embodiments, the DGAT polypeptide that is expressed in a cell is a DGAT2 polypeptide, such as a *Vernonia galamensis* DGAT2 polypeptide (see, e.g., GENBANK® Accession No. FJ652577, which is incorporated herein by this reference). In some embodiments, the DGAT2 polypeptide is encoded by a nucleic acid sequence of SEQ ID NO: 1.

In some embodiments of the presently-disclosed methods, the epoxygenase polypeptide is encoded by a nucleic acid sequence of SEQ ID NO: 5. In some embodiments, the epoxygenase polypeptide is a *Stokesia laevis* polypeptide, such as the epoxygenase described in U.S. Pat. No. 7,364,901, which is incorporated herein by this reference (see, also, GENBANK® Accession No. EA619792.1, which is further incorporated herein).

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See, e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Polynucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

The presently-disclosed subject matter is further illustrated by the following specific but non-limiting examples. Some of the following examples are prophetic, notwithstanding the numerical values, results and/or data referred to and contained in the examples.

EXAMPLES

Example 1

Cloning and Structural Analysis of a cDNA Encoding Diacylglycerol Acyltransferase 2 (DGAT2) from *Vernonia galamensis*

First strand cDNAs made from total RNA from developing *Vernonia galamensis* seeds were used for to clone the full-length diacylglycerol acyltransferase 2 (DGAT2) cDNA (SEQ ID NO: 3). Briefly, three pairs of degenerate primers were designed and used to amplify partial sequences from first-strand cDNAs derived from developing *Vernonia* seeds using low-stringency polymerase chain reaction (PCR) protocols. After several rounds of degenerate PCR, three fragments with different lengths were amplified. One amplicon (around 300 bp) was confirmed to share homology with known DGAT2 sequences (e.g., 81% identity to *Arabidopsis* DGAT2) at the DNA sequence level. This partial sequence was then used to design the primers for isolation of full-length cDNA sequences by 5' and 3' RACE (rapid amplification of cDNA ends). A full-length cDNA (designed as VgDGAT2; SEQ ID NO: 3) was then obtained and sub-cloned into the pGEM-T Easy plasmid according to the manufacturer's instructions, and the inserted cDNA was sequenced in both directions.

Database searches were also performed using the BLAST program at the National Center of Biotechnology Information. Alignments of the DNA or expected protein sequences were performed with MegAlign of DNASTAR® (DNASTAR Inc., Madison, Wis.) and the protein motifs were identified using PROSITE scan and Localizome.

Figure 1B:
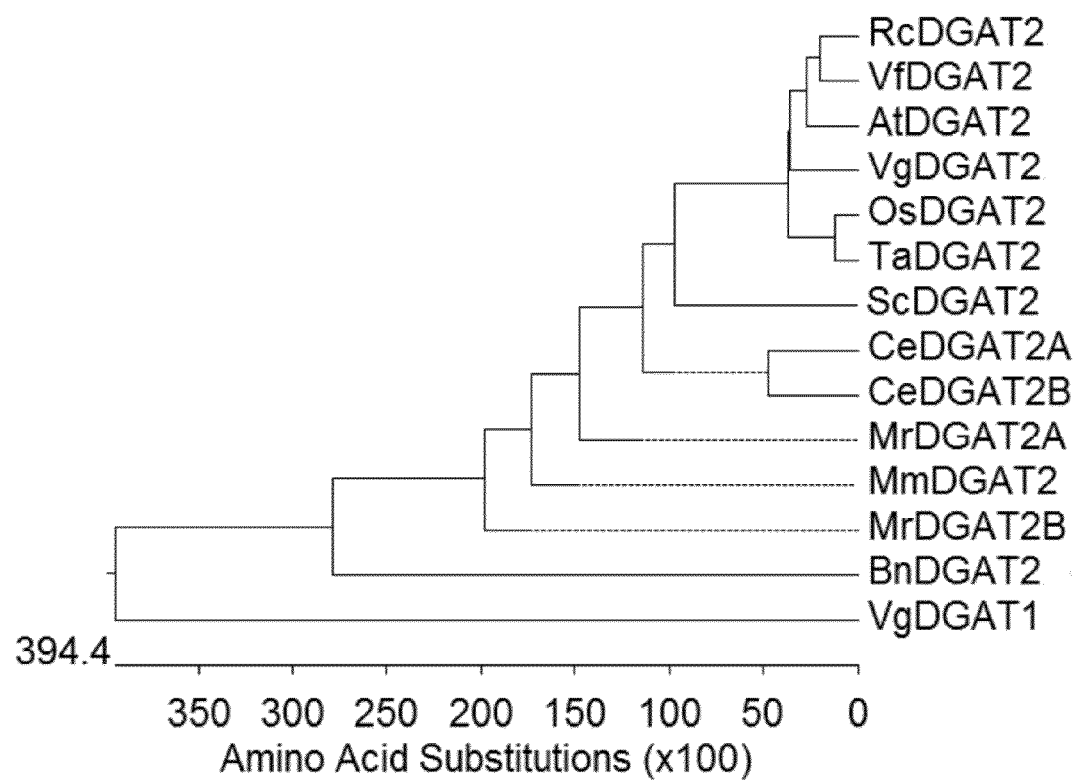

The full-length VgDGAT2 cDNA that was obtained by 5' and 3' RACE (SEQ ID NO: 3; GENBANK® BanKit No. 1176836) was found to be 1,212 bp in length and included 84 bp of a 5'-leader sequence and 111 bp of a 3'-untranslated region. The open reading frame was found to be 1, 017 bp in length (SEQ ID NO: 1) and was found to encode a protein of 338 amino acids (SEQ ID NO: 2). Alignment of the deduced amino acid sequences of DGAT2s from different species revealed that the proteins shared at least approximately 50% identity (FIGS. 1A and 1B). No homology was found between the VgDGAT2 amino acid sequence and the amino acid sequences of diacylglycerol acyltransferase 1 (DGAT1) peptides, including the DGAT1 sequences of *Vernonia galamensis* (VgDGAT1) and other species. A hydropathy plot of the VgDGAT2 amino acid sequence indicated that VgDGAT2 has two possible transmembrane regions located near the N-terminus of the sequence and in the region of amino acids 36-52 and 57-84 (FIG. 1A).

An alignment of multiple DGAT2 proteins was also used to identify potential retrieval motifs (FIG. 1A), and revealed that the DGAT2 proteins contain a motif, which is similar to a recently identified pentapeptide ER retrieval motif (McCarttney et al., 2004), and was positioned at the extreme C-terminus of the proteins. This ER motif was found to be "-LELKI-" (SEQ ID NO: 6) in VgDGAT2.

Example 2

VgDGAT 1a and VgDGAT2 Gene Expression in Developing *Vernonia* Seeds

To assess the gene expression of VgDGAT1a and VgDGAT2 in developing *Vernonia galamensis* seeds, primers for specific amplification of each cDNA were designed using Primer Express software (Applied Biosystems, Foster City, Calif.), taking into account criteria such as product length (around 500 bp), optimal PCR annealing temperature, and likelihood of primer self-annealing. The primers for specific amplification of VgDGAT1a and VgDGAT2 cDNA were designed to amplify the target cDNA at approximately 500 bp in length. The primers for VgDGAT1a were 5'-CCACCA-CAACTATAAGACGGCGGACCACTGT-3' (SEQ ID NO: 7; forward) and 5'-CTGAATCGAACCTCAGAATCAT-GAAGACCGG-3' (SEQ ID NO: 8; reverse). The primers for VgDGAT2 were 5'-CGAATCTTTAGTTATGTCAG-TAAATACGTTA-3' (SEQ ID NO: 9; forward) and 5'-TAAT-AGCCCTAGCCTTCAGTACGTAGAATTCG-3' (SEQ ID NO: 10; reverse). The primers for the actin gene (internal standard) were 5'-AGGGGATAACCACCCCAT-GAATCCA-3' (SEQ ID NO: 11; forward) and 5'-TGCATG-GTCTCCTGATACGGCCAAG-3' (SEQ ID NO: 12; reverse).

PCR reactions were performed in triplicate in 25 µL volumes using 1 µL of each forward and reverse primer (500 nM), 12.5 µL of SYBR® green master mix, 5 µL of a 1:10 (v/v) dilution of cDNA and 5.5 µL of DEPC treated water. Reactions were performed in MicroAmp 96-well plates (Applied Biosystems, Foster City, Calif.) covered with optical adhesive covers (Applied Biosystems, Foster City, Calif.). The following program was applied: initial polymerase activation at 95° C. for 10 min; then a two-temperature thermal cycle consisting of denaturation at 95° C. for 15 s, followed by annealing and extension at 60° C. for 1 min, with a total of 40 cycles.

To perform the PCR reactions, total RNA from roots, stems, leaves, pericarp, and developing seeds of *Vernonia galamensis* plants at six developmental stages (10, 17, 24, 31, 38 and 45 days after pollination (DAP)) was isolated, and then reverse transcribed to the first strand cDNA using the methods described above. The first-strand cDNA (5 µL) was used to amplify the target cDNA. All real-time reactions were performed in an iCycler iQ detection system (Bio-Rad, Hercules, Calif.) using the intercalation dye SYBR® Green I master mix kit (Applied Biosystems, Foster City, Calif.) as a fluorescent reporter. PCR reactions were performed in triplicate.

The quantification of PCR products was performed via a calibration curve procedure using the actin gene as an internal standard. PCR products were analyzed using melting curves as well as agarose gel electrophoresis to ensure single product amplification. The ratio of gene-specific expression to actin signal was defined as relative expression. PCR controls were performed in the absence of added reverse transcriptase to ensure RNA samples were free of DNA contamination.

Figure 2A:
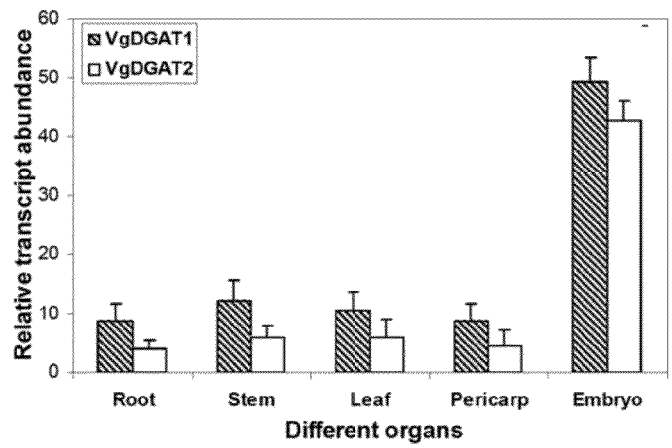
FIGS. 2A-2C are graphs showing the expression patterns of VgDGAT genes in relation to *Vernonia galamensis* seed oil synthesis, including: a graph showing VgDGAT1a (VgDGAT1) and VgDGAT2 gene expression in different organs of *Vernonia galamensis* (FIG. 2A); a graph showing VgDGAT1a (VgDGAT1) and VgDGAT2 gene expression during seed development in *Vernonia galamensis* (FIG. 2B); and a graph showing the accumulation of vernolic acid (percent of total fatty acid methyl esters) and total seed fatty acids (percent of dry weight) in developing seeds of *Vernonia galamensis* (FIG. 2C).

Upon analysis of the results from these experiments, it was observed that transcript levels of both VgDGATs were much higher in embryos (sampled at 20 DAP) than in root, stems, leaves and pericarp where their expressions were not much different except for slightly higher levels in stem and leaf (FIG. 2A). VgDAGT1a expression was higher than VgDGAT2 in sampled organs. Tissue-specific expression analyses indicated that both VgDGATs may be important for *Vernonia* seed oil biosynthesis.

Figure 2B:
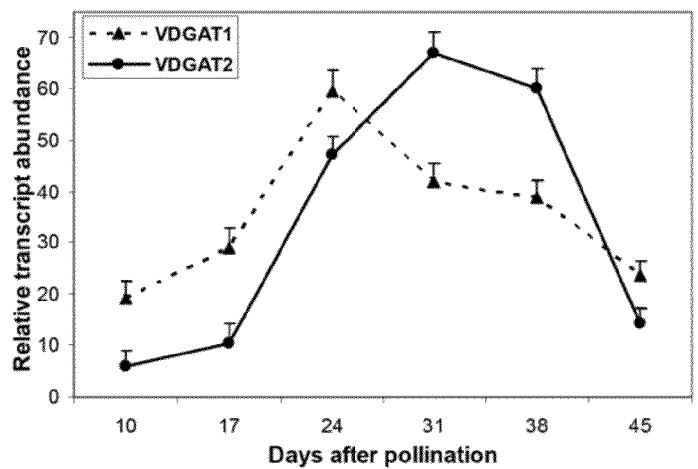
Figure 2C:
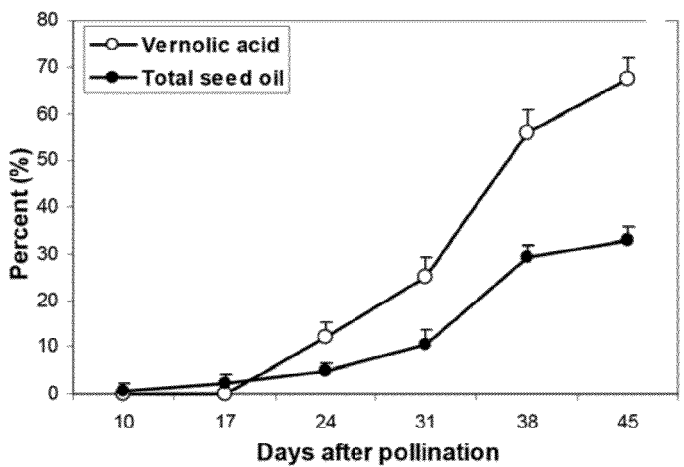

During seed development, VgDGAT1a transcripts moderately increased at early stages (from 10 to 17 DAP) and then sharply rose up to its peak level at 24 DAP (FIG. 2B). Subsequently, VgDGAT1a expression dropped gradually until 45 DAP. Similarly, VgDGAT2 mRNAs elevated at the greatest rate between 17 and 24 DAP and reached its highest level at 31 DAP (later than VgDGAT1a), followed by a slow decline from 31 to 38 DAP and then quickly decreasing. Compared to VgDGAT1a, the expression level of VgDGAT2 was higher at intermediate stages of development (between 24 and 38 DAP), a period during which both vernolic acid and total seed oil accumulate to 70% of their maximum levels (FIG. 2C). Notably, the highest rate of vernolic acid and total oil increase was between 31 and 38 DAP, which was two stages later than the maximum level of both VgDGAT mRNAs which was from 17 to 24 DAP (FIGS. 2B and 2C). Collectively, these data thus indicate that both VgDGATs contribute to the production of seed-specific triacylglycerols (TAGs) containing vernolic acid, with VgDGAT2 likely having a greater role.

Example 3

Co-Expression of VgDGAT with SlEPX in Agro-Infiltrated Petunia Leaves

To determine the effects of the co-expression of VgDGATs and *Stokesia laevis* epoxygenase genes (SlEPX) in agro-infiltrated petunia leaves, the coding regions of SlEPX (SEQ ID NO: 5), VgDGAT1a (SEQ ID NO: 4), and VgDGAT2 (SEQ ID NO: 1) were amplified with gene-specific primers containing recombination cloning sites, digested accordingly, and subsequently inserted between CaMV 35S promoter and NOS terminator in a modified pBI121 vector (Clontech, Palo Alto, Calif.) according to established protocols (Chen, et al., 2003). The recombinant binary pBI121 vector containing each of the target genes was then electroporated into an *Agrobacterium tumefaciens* cell strain GV3850 according the manufacturer's protocol (BioRad Laboratories, Hercules, Calif.).

The following agro-infiltrations were then performed as described previously (Wu, et al., 2005). Briefly, petunia leaves for experimental infiltration were chosen on the basis of size with a 5-cm width minimum. Leaves were either left on plants or cut from plants and rinsed in tap water to remove any adhering debris. Immediately prior to infiltration, detached leaves were placed on dampened paper towels in plastic boxes on the lab bench. Positive *A. tumefaciens* clones carrying the expression vector were maintained under kanamycin and rifampicin selection. Overnight cultures of single positive clones for infiltration were concentrated by brief centrifugation, and were resuspended in a 10% sucrose solution to a final concentration of $OD_{600}=0.5$ ($\pm 0.05$). The addition of 20 mM acetosyringone 3 h prior to infiltration enhanced plant expression in some experiments, but was not necessary. Petunia leaves were subsequently nicked on the lower leaf surface, and the bacterial suspension was then introduced using a needle-less syringe. For SlEPX/VgDGAT1a or SlEPX/VgDGAT2 co-expression in petunia leaves, the solution of *A. tumefaciens* clones containing the SlEPX expression vector was mixed 1:1 with the VgDGAT1a or VgDGAT2 expression vector. These mixed solutions were then used for infiltration.

During the experiments, the infiltrated plants were maintained in a greenhouse, while the detached petunia leaves of infiltration were maintained in an open plastic container on wet paper towels for up to 1 week at room temperature. Zones of infiltration were harvested with a sterile cork borer at 5 or 6 days after injection, and the resulting leaf discs were stored at −70° C. Experiments were repeated six times, and each gene construct was evaluated on 3 to 5 plants (3 leaves of each plant).

Without wishing to be bound by any particular theory, it was thought that if both VgDGATs function in the production of TAGs containing vernolic acid, co-expression of an epoxygenase gene, such as from *Stokesia laevis* (i.e., SlEPX), and either VgDGAT should lead to the enhancement of vernolic acid in the host tissues. To verify this, the agro-infiltration approach described above was used for in planta transient expression of either VgDGAT alone, or either VgDGAT combined with SlEPX.

Figure 3A:
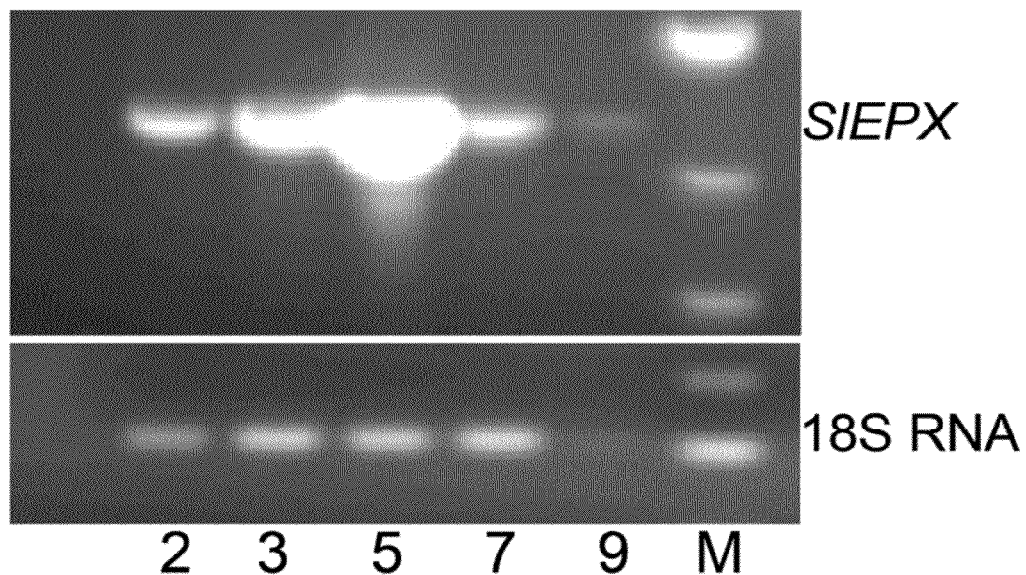
FIGS. 3A-3B are images of agarose gels showing the expression of transgenes in agro-infiltrated petunia leaves over time including: an image of a gel showing the time course of expression of a Stokesia laevis epoxygenase (SlEPX) transgene in agro-infiltrated petunia leaves at 2, 3, 5, 7, and 9 days after agro-infiltration (FIG. 3A); and, an image of an agarose gel showing reverse-transcriptase polymerase chain reaction (RT-PCR) recovery of VgDGAT2 transcripts in agro-infiltrated petunia leaves at 1, 2, 3, 4, and 5 days after agro-infiltration (FIG. 3B).
Figure 3B:
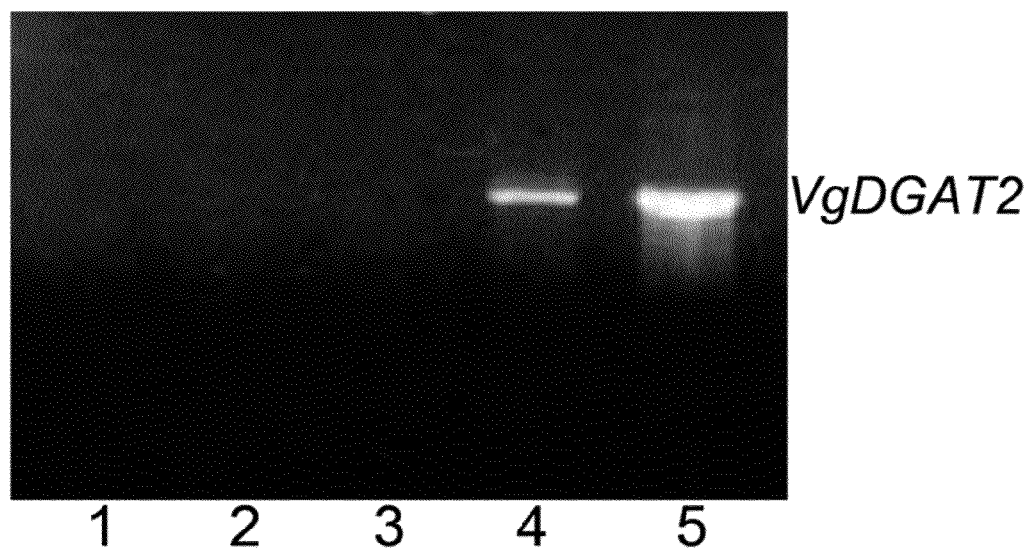

In these experiments, RT-PCR amplification of target cDNA from petunia leaf tissue agro-infiltrated with the transgenes was further used to assess the utility of this system for the generation of the expected transcripts (FIGS. 3A and 3B). Briefly, total RNA of the agro-infiltrated petunia leaf tissue was isolated using a standard isolation procedure and 5 µg of RNA was used for first-strand cDNA synthesis with an oligo (dT) primer. An aliquot of the first-strand synthesis reaction was then used in combination with transgene-specific primers.

Using these RT-PCR procedures, the time course for petunia mesophyll cells taking up and expressing the T-DNA-borne transgenes following agro-infiltration was first determined in leaf discs collected at 2, 3, 5, 7 and 9 days after agro-infiltration and tested for transgene expression by semi-quantitative RT-PCR (FIG. 3A). The introduced genes were expressed at low levels for the first 2 d after infiltration, then increased dramatically over the next 3 days. The maximum expression of the introduced genes was observed by 5 d post agro-infiltration and declined thereafter. Further experiments also revealed that templateless control, RNA from uninfiltrated and vector control infiltrated leaves showed no amplification product of the transgene, while the complete experimental reaction yielded the product of the transgene the as same as in the positive control of plasmid DNA template (FIG. 3B), thus indicating that the target transgenes expressed correctly in this system.

Based on the time course of the transgene expression, the agro-infiltrated petunia leaf tissues were then sampled at 5-6 d post infiltration for total lipid extraction and subsequently for thin layer chromatography (TLC) and gas chromatography (GC) analysis. Briefly, samples prepared as described above were frozen in liquid $N_2$, stored at −80° C. and then lyophilized. Weighed samples were transferred to glass test tubes and tri-heptadecanoin (tri-17:0) was then added at 10 µg/mg tissue as a standard. The samples were finely ground, and 1-2 mL of chloroform and methanol (2:1) containing 0.001% butylated hydroxytoluene (BHT) was added and samples ground further. After a brief spin, the lower layer ($CHCl_3$ phase) was subsequently transferred into a new glass tube. The samples were then divided into two aliquots, and one was used for TLC and the other directly for GC analysis.

For GC analysis, samples were then dried with $N_2$, and 0.5 mL of sodium methoxide ($NaOCH_3$) was then added and incubated for at least 15 minutes with shaking at 22° C. 0.5 mL of isooctane containing 0.001% BHT was added to each tube and mixed well. Phase separation was obtained with centrifugation or adding aqueous 0.9% KCl if needed. The top layer was extracted and transferred into GC auto-sampler vials. The fatty acid methyl esters (FAMEs) were analyzed with gas chromatography on a Varian CP-3800 GC with a 24 m×0.25 mm ID CP-Select CB for FAME fused silica column with a 0.25 µm film thickness. The temperature program was 90° C. for 1 min, then to 155° C. at 20° C./min with no hold, then to 175° C. at 3.6° C./min with no hold and finally to 250° C. at 12° C./min holding for one min.

For separation of individual lipid classes by TLC, the samples ($CHCl_3$ lipid extracts) were subsequently concentrated to about 50 to 100 µL. 10 µL of the sample was loaded in a narrow band in lanes of silica gel 60 TLC plates 1 cm from the bottom of the plates. The plates were put in a chamber with chloroform: methanol: water (65:25:4, v/v)+0.0001% BHT for running until the first solvent reached halfway up the plate (approximately 10 cm). Then, the plate was moved into the second solvent, hexane:diethyl ether:acetic acid (100:100:2, v/v)+0.0001% BHT and developed until solvent was approximately 1 cm from the top. After development, the plate was dried, and subsequently sprayed with 0.005% primulin in 80% acetone, followed by visualizing under UV light and marking the bands of interest. The bands were scraped transferred to a Pasteur pipette with a glass wool plug and washed with $CHCl_3:CH_3OH$. The lipid samples were eluted with 0.5 mL of $CHCl_3:CH_3OH+0.0001\%$ BHT twice. Finally, eluted lipid samples were dried, 0.5 mL sodium methoxide added and fatty acid methyl esters were prepared and analyzed by GC as described above.

Hydroxy/methoxy and trimethyl-silyl derivatives of epoxy fatty acids were also prepared as described previously (Cahoon, et al., 2002) with 2.5% sulfuric acid in methanol and bis-(trimethylsilyl) trifluoroacetamide: trimethylchlorosilane (99:1, v/v) (Supelco, Bellefonte, Pa.) with heating. GC-MS analyses were performed on an HP GCD GC-MS system with both HP-5 and Varian Factor Four VF-23MS capillary columns (30 m×0.25 mm, 0.25-µm phase thickness). 1 µL samples were injected in the splitless mode at 250° C. with an initial oven temperature of 100° C. for 1 min followed by a 15° C./min gradient to 160° C. (Ramp 1) and a 4° C./min gradient to 240° C. (Ramp 2). Samples were further analyzed using a Thermo Finnigan DSQ GC-MS system equipped with a Restec Rtx-5 (CROSSBOND® 5% diphenyl/95% dimethyl polysiloxane) capillary column (30 m×0.32 mm, 0.25-µm phase thickness). 1.5 µL samples were injected in the splitless mode at 250° C. with an initial oven temperature of 150° C. for 1 min followed by a 4° C./min gradient to 240° C. (Ramp 1), a 20° C./min gradient to 300° C. (Ramp 2), and 5 minutes at 300° C.

Figure 4A:
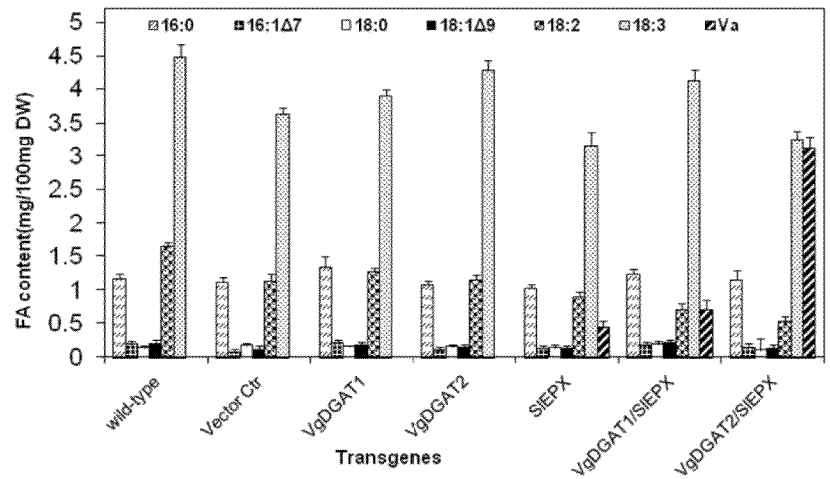
FIGS. 4A and 4B are graphs showing fatty acid profiles in agro-infiltrated petunia leaves (FIG. 4A) expressing a SlEPX transgene (SlEPX) alone or in combination with a VgDGAT1a transgene (VgDGAT1/SlEPX) or a VgDGAT2 transgene (VgDGAT2/SlEPX), and showing vernolic acid and total lipid contents in triacyglycerols (Total TAG) extracted from the agro-infiltrated petunia leaves (FIG. 4B).

Upon analysis of the results from these experiments, it was observed that vernolic acid was not detected in the non-agro-infiltrated and empty-vector-control leaves, but was present in the petunia leaves expressing epoxygenase alone and in petunia leaves co-expressing epoxygenase and either VgDGAT (FIG. 4A). Compared to the expression of SlEPX alone, VgDGAT1a co-expression increased vernolic acid level two-fold, and VgDGAT2 co-expression resulted in an enhancement of about five times more. Others have previously reported that transgenic plants expressing epoxygenases that accumulate vernolic acid also show readily detectable levels of the epoxygenation product of α-linolenic acid, 12-epoxy-Z9, Z15-octadecadienoic acid (12-epoxy-18:2Δ9,15) at levels as much as a third or more of the vernolic acid levels (Singh, et al., 2001 and Cahoon, et al. 2002). However, despite thorough analyses, little 12-epoxy-18:2Δ9,15 was found in any of the high vernolic acid accumulating plant tissues. With careful selective ion scans of GC-MS runs, 12-epoxy-18:2Δ9,15 was found at approximately 0.1% of the vernolic acid levels or at less than or equal to 0.04% of total fatty acids.

Figure 4B:
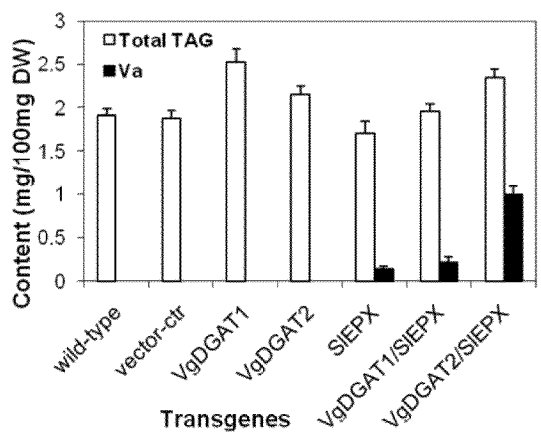

To further examine whether the newly synthesized vernolic acids were in TAGs, TLC was used to separate TAG from other lipid classes, and fatty acid profiles in TAG were analyzed by GC. From these experiments, it was clear that vernolic acid was found in the leaves expressing SlEPX alone or with each VgDGAT while no vernolic acid was detected in the control samples and leaves only expressing either VgDGAT1a or VgDGAT2 (FIG. 4B). Furthermore, it was evident that vernolic acid accumulated to a much higher level in the VgDGAT2-co-expressing leaves than in the SlEPX-only expressing samples or in the VgDGAT1a-co-expressing samples.

Experiments are also performed with agro-infiltrated petunia leaves co-expressing SlEPX and VgDGAT1b. Similarly to the experiments described above, nucleic acid sequences including SlEPX and VgDGAT1b (SEQ ID NO: 17) coding regions are inserted into a suitable plasmid and then electroporated into an *Agrobacterium tumefaciens* cell strain prior to agro-infiltrating positive *A. tumefaciens* clones into petunia leaves. Both nucleic acid sequences express correctly in the leaves and an increase in epoxy fatty acid accumulation, including levels of vernolic acid, is observed in the agro-infiltrated leaves, indicating that a method including expressing a DGAT1b and an EPX transgene is useful in increasing an amount of epoxy fatty acid in a cell.

Example 4

Co-Expression of VgDGAT with SlEPX in Soybean Somatic Embryos

To determine the effects of co-expression of VgDGATs and SlEPX in soybean somatic embryos, an expression vector for soybean transformation was constructed using the plant expression vector pCAMBIA1301, which contained the hygromycin resistance gene as a selector and the GUS gene as a reporter (Cambia, ACT, Australia; GENBANK® Accession No. AF234297). The coding sequences of SlEPX, VgDGAT1a and VgDGAT2 were amplified by a high fidelity polymerase (Invitrogen, Carlsbad, Calif.) using end-specific primers containing restriction sites. The amplification product was then sub-cloned into the respective sites of a pPHI4752 vector containing a phaseolin promoter, which confers seed-specific expression of transgenes (see, Slightom et al., 1983). The phaseolin promoter cassette containing the coding region of each target gene was then transferred into the corresponding sites of the binary pCAMBIA1301, T-DNA vector. These recombinant expression vectors were subsequently introduced into somatic embryos of soybean (cv. 'Jack') using the particle bombardment method of transformation.

In this regard, soybean somatic embryo induction and culture was carried out using a protocol modified from prior procedures, (Collins et al., 1991; Finer and Nagasawa, 1988; Samoylov et al., 1998; Trick et al., 1997). Briefly, immature soybean seeds at 3-5 mm length were dissected, and cotyledons were placed on D40 solid medium for one-month induction. The induced embryos were transferred to D20 plates for proliferation. The globular embryogenic cultures from D20 plates were then moved into FN liquid medium for one-month suspension culture. Small embryo clumps were selected for shooting.

Figure 5:
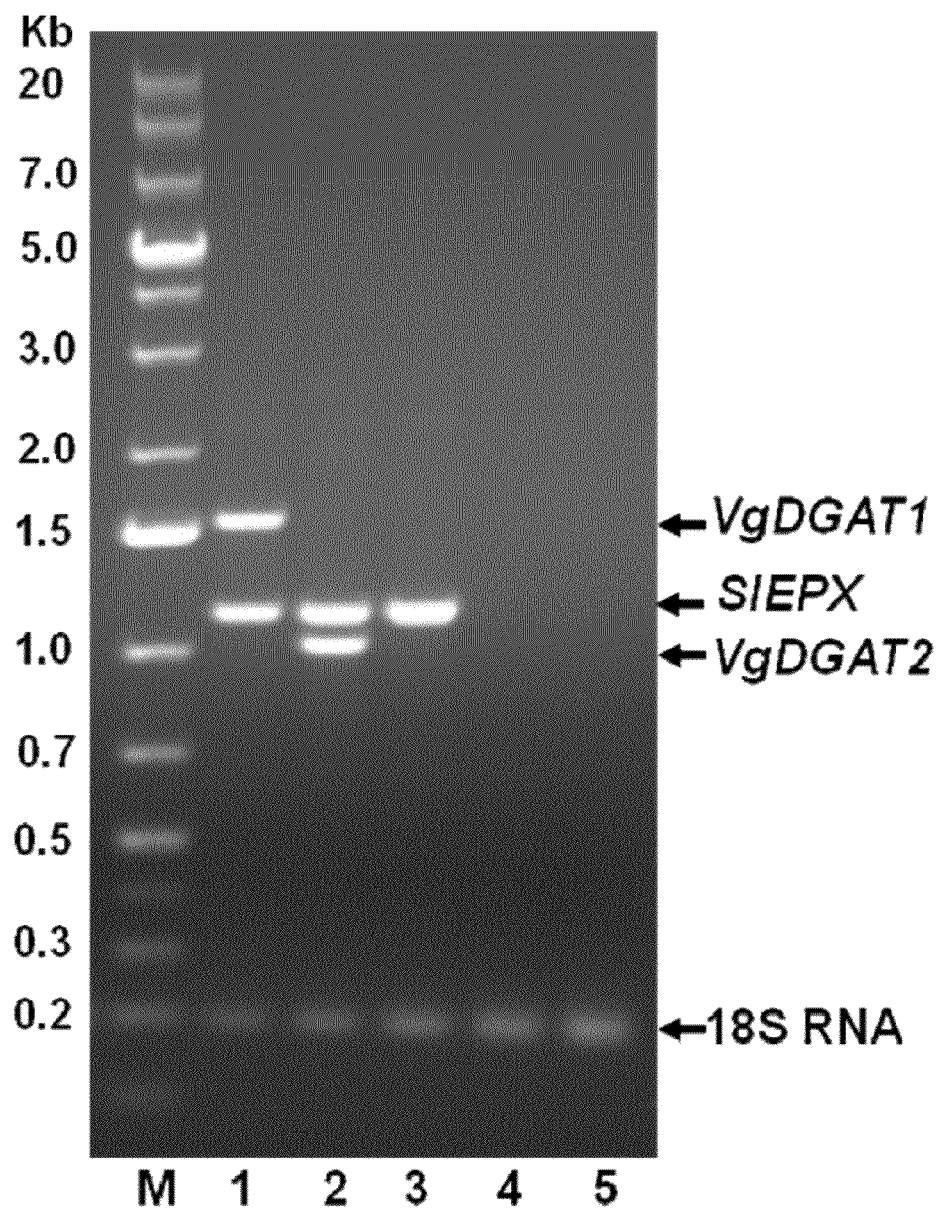
FIG. 5 is an image of an agarose gel showing a transcript analysis of transgenic soybean somatic embryos expressing either: a VgDGAT1a (VgDGAT1) transgene and a SlEPX transgene (Lane 1); a VgDGAT2 transgene and a SlEPX transgene (lane 2); or a SlEPX transgene (Lane 3). Lanes 4 and 5 included samples from a vector-control line and an untransformed line, respectively, and M indicates a DNA ladder.

Plasmid DNA/gold preparation for the particle bombardment was then conducted according to standard protocols (Trick et al., 1997). A DuPont Biolistic PDS1000/HE instrument (helium retrofit) was used for all transformations. After shooting, the embryo clumps were transferred into FN liquid medium containing 30 mg/L hygromycin for selective culture for four to five weeks. The positive transformed embryos obtained by hygromycin selection were then moved into fresh FN liquid medium for culture and simultaneously for GUS test and identification of the transgene presence by PCR (see, FIG. 5). The PCR-positive transgenic embryo lines were then transferred into maturation medium (SHaM; Schmidt et al., 2005) for three to five weeks. Matured individual embryos were desiccated for 4-7 days, and then were placed on half-strength MS solid medium for germination. Germinated plantlets were transferred to closed sterile soil cups for growth in a culture room under 23:1 (light:dark) photoperiod cycle and 25° C. Once the seedlings reached a proper height (approximately 13 cm), they were then transferred to a greenhouse for flowering and seed set under a 16:8 (light:dark) cycle, 25/21° C.

For the transgenic lines, one set of matured somatic embryos were sampled for lipid extraction and subsequent GC analysis. The rest of the matured somatic embryos were desiccated, germinated and grown to maturity in a greenhouse. Mature seeds were harvested from each regenerated soybean plant separately. Seeds were chipped for genotyping by PCR and fatty acid analysis by GC.

Upon analysis of the results, it was observed that vernolic acid levels in transgenic somatic embryo lines were 5.0±0.6%, 9.1±0.5% and 17.6±0.9% (w/w) for lines expressing SlEPX expression alone, co-expressing SlEPX with VgDGAT1, or co-expressing SlEPX with VgDGAT2, respectively (Table 1). However, no vernolic acid was found in the vector control lines or in either of the VgDGAT-expressing lines. Interestingly, the accumulation of vernolic acid was accompanied by decrease in linoleic acid (C18:2) and α-linolenic acid (C18:3) levels and a slight increase in the oleic acid (C18:1) content in SlEPX lines compared to empty vector-transformed embryos. C18:2 and C18:3 were also reduced in SlEPX/VgDGAT transgenic lines with no changes for other fatty acids in the double-transgenic lines. VgDGATs, particularly VgDGAT2, enhanced vernolic acid accumulation in soybean somatic embryos.

TABLE 1

Fatty acid profiles in mature soybean somatic embryos of vector control, SlEPX- and SlEPX /VgDGAT-expressed lines (% of total fatty acids).

|  | 16:0 | 18:0 | 18:1 | 18:2 | 18:3 | Vernolic acid |
|---|---|---|---|---|---|---|
| Vector-control lines | 14.3 ± 0.2 | 3.8± 0.1 | 8.7± 0.6 | 56.2± 0.8 | 16.8± 0.6 | ND |
| SlEPX transgenic lines | 12.9 ± 0.2 | 4.9± 0.2 | 13.1± 0.2 | 47.8± 1.2 | 14.9± 0.8 | 5.0± 0.6 |
| Co-expressing SlEPX + VgDGAT1a lines | 15.7 ± 0.3 | 4.6± 0.2 | 10.3± 0.5 | 45.4± 1.5 | 14.6± 0.7 | 9.1± 0.5 |
| Co-expressing SlEPX + VgDGAT2 lines | 13.6 ± 0.26 | 3.5± 0.2 | 9.1± 0.5 | 43.3± 1.0 | 12.2± 0.5 | 17.6± 0.9 |

Experiments are also performed with soybean somatic embryos co-expressing SlEPX and VgDGAT1b. Similarly to the experiments described above, nucleic acid sequences including SlEPX and VgDGAT1b (SEQ ID NO: 17) coding regions are inserted into a suitable expression vector and introduced into soybean somatic embryos using the particle bombardment method of transformation. Both nucleic acid sequences express correctly in the soybean somatic embryos and an increase in epoxy fatty acid accumulation, including levels of vernolic acid, is observed in the soybean embryos, indicating that a method including expressing a DGAT1b and an EPX transgene is useful in increasing an amount of epoxy fatty acid in a cell.

Example 5

Figure 6:
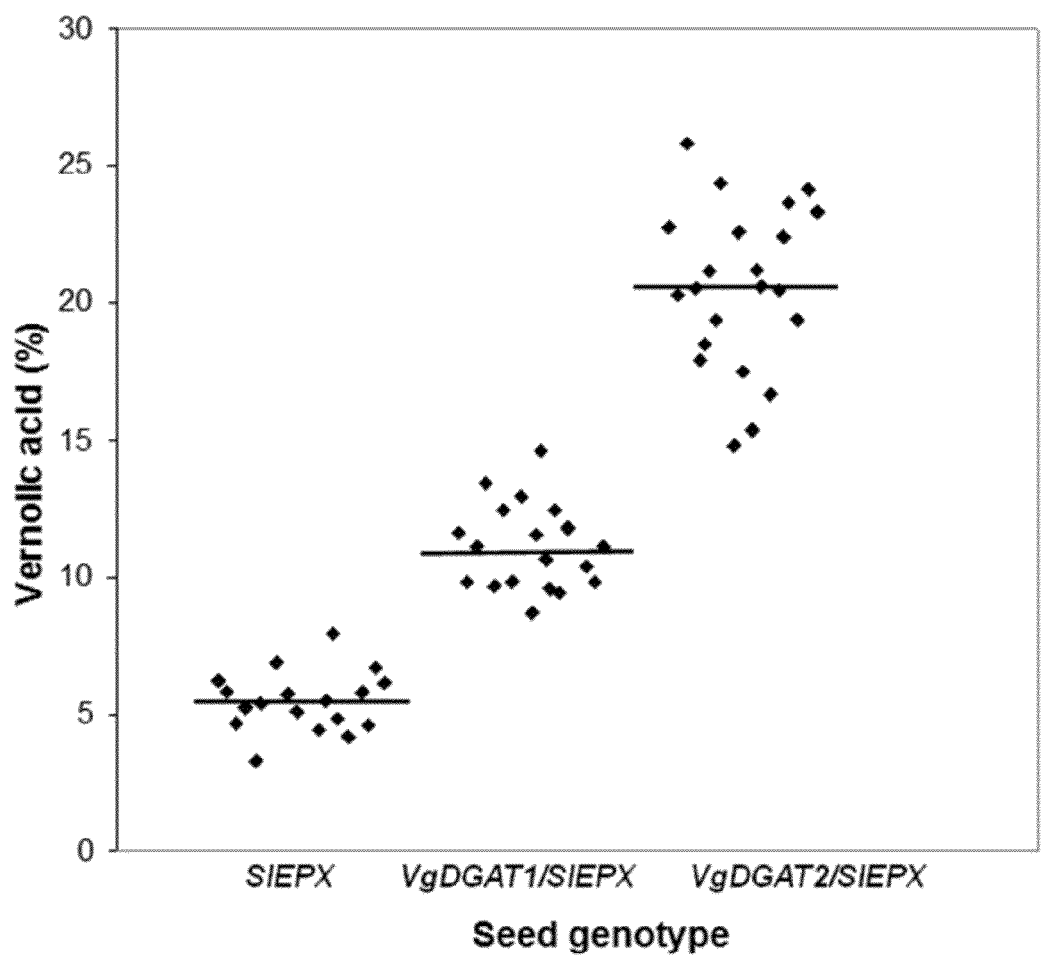
FIG. 6 is a graph showing vernolic acid contents of transgenic soybean seeds from regenerated plants expressing either: a SlEPX transgene (SlEPX); a VgDGAT1a transgene and a SlEPX transgene (VgDGAT1/SlEPX); or a VgDGAT2 transgene and a SlEPX transgene (VgDGAT2/SlEPX).
Figure 7:
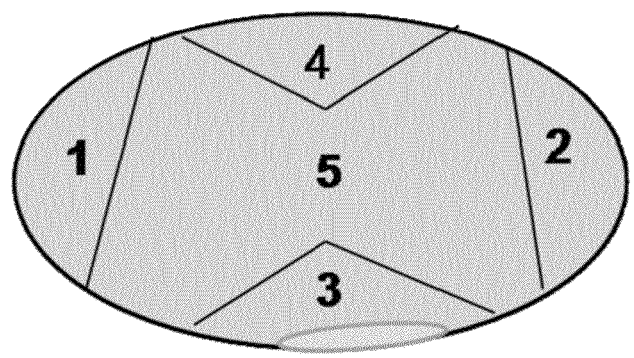
FIG. 7 includes a schematic diagram and a table showing the vernolic acid (Va) content in different sections of soybean seeds expressing a SlEPX transgene and a VgDGAT2 transgene, where the seeds were divided into five sections, as indicated, and each section was analyzed for vernolic acid content.

Levels of Vernolic Acid in Mature Seeds of Regenerated Transgenic Soybeans Obtained by Co-Expressing SlEPX with VgDGATs To assess the levels of vernolic acid in mature seeds of regenerated transgenic soybeans, the transgenic soybean somatic embryos were germinated and grown to maturity in a greenhouse. Seed-chips of each progeny seed collected from the regenerated transgenic soybean plants were then sampled for fatty acid analysis by GC and genotyping by PCR. Vernolic acid was detected in the SlEPX-transgenic seeds and double-transgenic seeds expressing SlEPX with a VgDGAT, but not in the seeds of null-transgenic segregants, vector control lines, or the VgDGAT1a- or VgDGAT2-single transgenic lines (Table 2 and FIG. 6). Vernolic acid content in SlEPX-transgenic seeds ranged from 2.5% to 7.9% with an average of 5.5%. In SlEPX/VgDGAT1a double-transgenic seeds, the highest accumulation of vernolic acid was 14.6% with an average of 11.1%. The maximum level of vernolic acid was 25.8% with an average of 20.6%, which was found in the SlEPX/VgDGAT2 double-transgenic seeds. No readily detectable 12-epoxy-18:2Δ9,15 (<0.05% total fatty acids) were found in soybean seeds even with vernolic acid levels of greater than 25%. Furthermore, the vernolic acid levels were uniform in the different seed parts (FIG. 7). These data thus demonstrated that VgDGATs, especially VgDGAT2, can increase accumulation of vernolic acid in soybean seed oil.

TABLE 2

Fatty acid profiles in soybean seed oil from wild type, vector control, SlEPX- and SlEPX/VgDGAT-transgenic soybean plants (% of total fatty acids)

|  | 16:0 | 18:0 | 18:1 | 18:2 | 18:3 | Vernolic acid |
|---|---|---|---|---|---|---|
| Non-transgenic line | 9.6 | 3.9 | 11.4 | 62.2 | 11.0 | ND |
| Vector-control line | 11.8 | 4.5 | 12.7 | 59.8 | 9.9 | ND |
| Null segregant | 10.9 | 3.1 | 10.9 | 60.9 | 13.7 | ND |
| SlEPX transgenic line (9996-6-1-5) | 5.7 | 6.1 | 16.8 | 53.1 | 8.6 | 7.9 |
| Co-expressing SlEPX + VgDGAT1a line (9384-1-2-1) | 9.2 | 4.6 | 13.3 | 49.4 | 8.9 | 14.6 |
| Co-expressing SlEPX + VgDGAT2 line (9994-2-2-4) | 7.9 | 3.1 | 9.5 | 46.1 | 7.2 | 25.8 |

In addition, the expression of transgenes caused some changes in fatty acid profiles in soybean seed oil compared to those in wild-type and vector control seeds. In SlEPX-containing seeds, C18:1 increased some, whereas C18:2 was reduced considerably and C18:3 slightly decreased. Likewise, in SlEPX/VgDGAT-containing seeds, C18:2 and C18:3 decreased. Higher accumulation of vernolic acid was associated with lower C18:2. Again, however, data from mature transgenic soybean seeds revealed that VgDGATs, particularly VgDGAT2, are able to increase the accumulation of vernolic acid in soybean seed oil.

Throughout this document, various references are mentioned. All such references are incorporated herein by reference, including the references set forth in the following list:

REFERENCES

1. Bafor M, Smith M A, Jonsson L, Stobart K and Stymme S (1993) Biosynthesis of vernoleate (cis-12-epoxyoctadeca-cis-9-enoate) in microsomal preparations from developing endosperm of *Euphorbia lagascae*. *Archives of Biochemistry and Biophysics* 303:145-151.
2. Burgal J, Shockey J, Lu C, Dyer J, Larson T, Graham I and Browse J (2008) Metabolic engineering of hydroxy fatty acid production in plants: RcDGAT2 drives dramatic increases in ricinoleate levels in seed oil. *Plant Biotechnology Journal* 8:819-831.
3. Cahoon E B, Dietrich C R, Meyer K, Damude H G, Dyer J M and Kinney A J (2006) Conjugated fatty acids accumulate to high levels in phospholipids of metabolically engineered soybean and *Arabidopsis* seeds. *Phytochemistry* 67:1166-1176.

4. Cahoon E B, Hitz W D and Ripp K G (2001) Plant genes for fatty acid modifying enzymes (FAD2) associated with conjugated double bond formation and transgenic plants having altered lipid profiles, in World Patent Application.
5. Cahoon E B, Ripp K G, Hall S E and McGonigle B (2002) Transgenic production of epoxy fatty acids by expression of a cytochrome P450 enzyme from *Euphorbia lagascae* seed. *Plant Physiology* 128:615-624.
6. Cahoon E B, Shockey J M, Dietrich C R, Gidda S K, Mullen R T and Dyer J M (2007) Engineering oilseeds for sustainable production of industrial and nutritional feedstocks: solving bottlenecks in fatty acid flux. *Current Opinion in Plant Biology* 10:236-244.
7. Cases S, Stone S J, Zhou P, Yen E, Tow B, Lardizabal K D, Voelker T and Farese R V, Jr. (2001) Cloning of DGAT2, a Second Mammalian Diacylglycerol Acyltransferase, and Related Family Members. *J Biol Chem* 276:38870-38876.
8. Chen P-Y, Wang C-K, Soong S-C and To K-Y (2003) Complete sequence of the binary vector pBI121 and its application in cloning T-DNA insertion from transgenic plants. *Molecular Breeding* 11:287-293.
9. Collins G B, Hildebrand D F, Lazzeri P A, Adams T R, Parrott W A and Hartweck L M (1991) Transformation, somatic embryogenesis and whole plant regeneration method for Glycine species, United States: University of Kentucky.
10. Finer J J and Nagasawa A (1988) Development of an embryogenic suspension culture of soybean (*Glycine max* Merrill.). *Plant Cell Tissue and Organ Culture* 15:125-136.
11. Hatanaka T, Shimizu R and Hildebrand D (2004) Expression of a *Stokesia laevis* epoxygenase gene. *Phytochemistry* 65:2189-2196.
12. He X, Turner C, Chen G, Lin J-T and Mckeon T (2004) Cloning and characterization of a cDNA encoding diacylglycerol acyltransferase from castor bean. *Lipids* 39:311-318.
13. Jako C, Kumar A, Wei Y, Zou J, Barton D L, Giblin E M, Covello P S and Taylor D C (2001) Seed-Specific Over-Expression of an *Arabidopsis* cDNA Encoding a Diacylglycerol Acyltransferase Enhances Seed Oil Content and Seed Weight. *Plant Physiol* 126:861-874.
14. Jaworski J and Cahoon E B (2003) Industrial oils from transgenic plants. *Current Opinion in plant Biology* 6:178-184.
15. Kroon J T M, Wei W, Simon W J and Slabas A R (2006) Identification and functional expression of a type 2 acyl-CoA:diacylglycerol acyltransferase (DGAT2) in developing castor bean seeds which has high homology to the major triglyceride biosynthetic enzyme of fungi and animals. *Phytochemistry* 67:2541-2549.
16. Lardizabal K D, Mai J T, Wagner N W, Wyrick A, Voelker T and Hawkins D J (2001) DGAT2 is a new diacylglycerol acyltransferase gene family. Purification, cloning, and expression in insect sells of two polypeptides from *Mortierella ramanniana* with diacylglycerol acyltransferase activity. *J Biol Chem* 276:38862-38869.
17. Lee M, Lenman M, Banas A, Bafor M, Singh S, Schweizer M, Nilsson R, Liljenberg C, Dahlqvist A, Gummeson P O, Sjodahl S, Green A and Stymne S (1998) Identification of non-heme diiron proteins that catalyze triple bond and epoxy group formation. *Science* 280:915-918.
18. Lee S, Lee B, Jang I, Kim S and Bhak J (2006) Localizome: a server for identifying transmembrane topologies and TM helices of eukaryotic proteins utilizing domain information. *Nucl Acids Res* 34:W99-W103.
19. Li R, Yu K and Hildebrand D F (2009) DGAT1, DGAT2 and PDAT Expression in Seeds and Other Tissues of Epoxy and Hydroxy Fatty Acid Accumulating Plants. *Lipids In review*.
20. Lung S-C and Weselake R (2006) Diacylglycerol acyltransferase: a key mediator of plant triacylglycerol synthesis. *Lipids* 41:1073-1088.
21. McCarttney A W, Dyer J M, Dhanoa P, Kim P K, Andrews D Y, McNew J A and Mullen R T (2004) Membrane-bound fatty acid desaturase are inserted co-translationally into the ER and contain different ER retrieval motifs at their carboxy termini. *Plant Journal* 37:156-173.
22. Pascual M J and Correal E (1992) Mutation studies of an oilseed spurge rich in vernolic acid. *Crop Science* 32:95-98.
23. Perdue R E (1989) *Vernonia*—bursting with potential. *Agricultural Engineering* 70:11-13.
24. Saha S, Enugutti B, Rajakumari S and Rajasekharan R (2006) Cytosolic Triacylglycerol Biosynthetic Pathway in Oilseeds. Molecular Cloning and Expression of Peanut Cytosolic Diacylglycerol Acyltransferase. *Plant Physiology* 141:1533-1543.
25. Samoylov V M, Tucker D M and Parrott W A (1998) A liquid medium-based protocol for rapid regeneration from embryogenic soybean cultures. *Plant Cell Reports* 18:49-54.
26. Schmidt M, Tucker D, Cahoon E and Parrott W (2005) Towards normalization of soybean somatic embryo maturation. *Plant Cell Reports* 24:383-391.
27. Shockey J M, Gidda S K, Chapital D C, Kuan J-C, Dhanoa P K, Bland J M, Rothstein S J, Mullen R T and Dyer J M (2006) Tung Tree DGAT1 and DGAT2 Have Nonredundant Functions in Triacylglycerol Biosynthesis and Are Localized to Different Subdomains of the Endoplasmic Reticulum. *Plant Cell* 18:2294-2313.
28. Siloto, R. M. P., M. Truksa, X. H. He, T. McKeon, and R. J. Weselake. 2009. Simple Methods to Detect Triacylglycerol Biosynthesis in a Yeast-Based Recombinant System. *Lipids* 44:963-973
29. Siloto, R. M. P., M. Truksa, D. Brownfield, A. G. Good, and R. J. Weselake. 2009. Directed evolution of acyl-CoA:diacylglycerol acyltransferase: Development and characterization of *Brassica napus* DGAT1 mutagenized libraries. Elsevier France-Editions Scientifiques Medicales Elsevier.
30. Singh S, Thomaeus S, Lee M, Stymne S and Green A (2001) Transgenic expression of a D12-epoxygenase gene in Arabidopsis seeds inhibits accumulation of linoleic acid. *Planta* 212:872-879.
31. Singh S P, Zhou X-R, Liu Q, Stymne S and Green A G (2005) Metabolic engineering of new fatty acids in plants. *Current Opinion in Plant Biology* 8:197-203.
32. Slightom J L, Sun S M and Hall T C (1983) Complete nucleotide sequence of a french bean storage protein gene: phaseolin. *Proc Natl Acad Sci USA* 80:1897-1901.
33. Spitzer V, Tomberg W and Zucolotto M (1996) Identification of α-parinaric acid in the seed oil of *Sebastiana brasiliensis* Sprengel (*Euphorbiaceae*). *Journal of the American Oil Chemists' Society* 73:569-573.
34. Stone S J, Levin M C and Farese R V, Jr. (2006) Membrane Topology and Identification of Key Functional Amino Acid Residues of Murine Acyl-CoA:Diacylglycerol Acyltransferase-2. *J Biol Chem* 281:40273-40282.
35. Thelen J J and Ohlrogge J B (2002) Metabolic engineering of fatty acid biosynthesis in plants. *Metabolic Engineering* 4:12-21.

36. Thompson A E, Dierig D A and Kleiman R (1994) Variation in *Vernonia galamensis* flowering characteristics, seed oil and vernolic acid contents. *Industrial Crops and Products* 3:175-183.
37. Trick F I N, Dinkins R D, Santarem E R, Di R, Samoylov V M, Meurer C, Walker D, Parrott W A, Finer J J and Collins G B (1997) Recent advances in soybean transformation. *Plant Tissue Culture and Biotechnology* 3:9-26.
38. van de Loo F J, Fox B G and Somerville C (1993) Unusual fatty acids, in Lipid Metabolism in Plants (Moore J T S ed) pp 91-126, Boca Raton: CRC Press.
39. Vogel G and Browse J (1996) Choline phospho transferase and diacylglycerol acyl transferase:substrate specificities at a key branch point in seed lipid metabolism. *Plant Physiology* 110:923-931.
40. Wu S, Schoenbeck M A, Greenhagen4 BT, Takahashi S, Lee S, Coates R M and Chappell J (2005) Surrogate Splicing for Functional Analysis of Sesquiterpene Synthase Genes. *Plant Physiology* 138:1322-1333.
41. Xu, J. Y., T. Francis, E. Mietkiewska, E. M. Giblin, D. L. Barton, Y. Zhang, M. Zhang, and D. C. Taylor. 2008. Cloning and characterization of an acyl-CoA-dependent diacylglycerol acyltransferase 1 (DGAT1) gene from *Tropaeolum majus*, and a study of the functional motifs of the DGAT protein using site-directed mutagenesis to modify enzyme activity and oil content. Plant Biotechnology Journal 6:799-818.
42. Yu K, Li R, Hatanaka T and Hildebrand D (2008) Cloning and functional analysis of two type 1 diacylglycerol acyltransferases from *Vernonia galamensis*. *Phytochemistry* 69:1119-1127.
43. Yu K, McCracken C J, Li R and Hildebrand D F (2006) Diacylglycerol acyltransferase from *Vernonia* and *Stokesia* prefer substrates with vernolic acid. *Lipids* 41:557-566.
44. Zhou X-R, Singh S and Green A (2008) Increased accumulation of epoxy fatty acids in Arabidopsis by transgenic expression of TAG assembly genes from *Bernardia pulchella*, in 18th International Symposium on Plant Lipids, Bordeaux, France.
45. Zhou X-R, Singh S, Liu Q and Green A (2006) Combined transgenic expression of Δ12-desaturase and Δ12-epoxygenase in high linoleic acid seeds leads to increased accumulation of vernolic acid. *Functional Plant Biology* 33:585-592.
46. U.S. Pat. No. 4,459,355 to Cello, et al., issued Jul. 10, 1984, and entitled "Method for transforming plant cells."
47. U.S. Pat. No. 4,536,475 to Anderson, issued Aug. 20, 1985, and entitled "Plant vector."
48. U.S. Pat. No. 4,683,195 to Mullis, et al., issued Jul. 28, 1987, and entitled "Process for amplifying, detecting, and/or-cloning nucleic acid sequences."
49. U.S. Pat. No. 4,945,050 to Sanford, et al., issued Jul. 31, 1990, and entitled "Method for transporting substances into living cells and tissues and apparatus therefore."
50. U.S. Pat. No. 5,036,006 to Sanford, et al., issued Jul. 30, 1991, and entitled "Method for transporting substances into living cells and tissues and apparatus therefore."
51. U.S. Pat. No. 5,100,792 to Sanford, et al., issued Mar. 31, 1992, and entitled "Method for transporting substances into living cells and tissues."
52. U.S. Pat. No. 5,177,010 to Goldman, et al., issued Jan. 5, 1993, and entitled "Process for transforming corn and the products thereof"
53. U.S. Pat. No. 5,179,022 to Sanford, et al., issued Jan. 12, 1993, and entitled "Biolistic apparatus for delivering substances into cells and tissues in a non-lethal manner."
54. U.S. Pat. No. 5,187,073 to Goldman, et al., issued Feb. 16, 1993, and entitled "Process for transforming gramineae and the products thereof"
55. U.S. Pat. No. 5,204,253 to Sanford, et al., issued Apr. 20, 1993, and entitled "Method and apparatus for introducing biological substances into living cells."
56. U.S. Pat. No. 5,371,014 to Matsuyama, et al., issued Dec. 6, 1994, "Process for the production of optically active 2-hydroxy acid esters using microbes to reduce the t-oxo precursor."
57. U.S. Pat. No. 5,405,765 to Vasil, et al., issued Apr. 11, 1995, and entitled "Method for the production of transgenic wheat plants."
58. U.S. Pat. No. 5,464,763 to Schilperoort, et al., issued Nov. 7, 1995, and entitled "Process for the incorporation of foreign DNA into the genome of dicotyledonous plants."
59. U.S. Pat. No. 5,478,744 to Sanford, et al., issued Dec. 26, 1995, and entitled "Method for transporting substances into living cells and tissues and apparatus therefore."
60. U.S. Pat. No. 5,484,956 to Lundquist, et al., issued Jan. 16, 1996, and entitled "Fertile transgenic *Zea mays* plant comprising heterologous DNA encoding *Bacillus thuringiensis* endotoxin."
61. U.S. Pat. No. 5,489,520 to Adams, et al., issued Feb. 6, 1996, and entitled "Process of producing fertile transgenic *zea mays* plants and progeny comprising a gene encoding phosphinothricin acetyl transferase."
62. U.S. Pat. No. 5,508,468 to Lundquist, et al., issued Apr. 16, 1996, and entitled "Fertile transgenic corn plants."
63. U.S. Pat. No. 5,510,318 to Patel, et al., issued Apr. 23, 1996, and entitled "Herbicidal oxazine ethers."
64. U.S. Pat. No. 5,538,877 to Lundquist, et al., issued Jul. 23, 1996, and entitled "Method for preparing fertile transgenic corn plants."
65. U.S. Pat. No. 5,554,798 to Lundquist, et al., issued Sep. 10, 1996, and entitled "Fertile glyphosate-resistant transgenic corn plants."
66. U.S. Pat. No. 5,565,346 to Facciotti, issued Oct. 15, 1996, and entitled "Transformation and regeneration system for legumes."
67. U.S. Pat. No. 7,364,901 to Hildebrand, et al., issued Apr. 29, 2008, and entitled "Recombinant Stokesia Epoxygenase Gene."
68. European Patent No. 267,159.
69. European Patent No. 604,662.
70. European Patent No. 672,752.
71. European Patent No. 442,174.
72. European Patent No. 486,233.
73. European Patent No. 486,234.
74. European Patent No. 539,563.
75. European Patent No. 674,725.
76. International Patent Application Publication No. WO 91/02071.
77. International Patent Application Publication No. WO 95/06128.
78. Batzer et al. (1991) *Nucleic Acid Res* 19: 5081.
79. Ohtsuka et al. (1985) *J Biol Chem* 260: 2605-2608.
80. Rossolini et al. (1994) *Mol Cell Probes* 8:91-98.
81. Karlin and Altschul. *Proc Natl Acad Sci USA* 87: 2264-2268, 1990, modified as in *Proc Natl Acad Sci* USA 90:5873-5877, 1993.
82. Altschul, et al. J. Mol. Biol. 215: 403-410, 1990.
83. Molecular Cloning A Laboratory Manual (1989), 2nd Ed., Sambrook, Fritsch and Maniatis, eds., Cold Spring Harbor Laboratory Press, Chapters 16 and 17.
84. DNA Cloning, Volumes I and II, Glover, ed., 1985.
85. Polynucleotide Synthesis, M. J. Gait, ed., 1984.

86. Nucleic Acid Hybridization, D. Hames & S. J. Higgins, eds., 1984.
87. Transcription and Translation, B. D. Hames & S. J. Higgins, eds., 1984.
88. Culture Of Animal Cells, R. I. Freshney, Alan R. Liss, Inc., 1987.
89. Immobilized Cells And Enzymes, IRL Press, 1986.
90. Perbal (1984), A Practical Guide To Molecular Cloning. Academic Press, Inc., N.Y.
91. Gene Transfer Vectors For Mammalian Cells, J. H. Miller and M. P. Calos, eds., Cold Spring Harbor Laboratory, 1987.
92. Methods In Enzymology, Vols. 154 and 155, Wu et al., eds., Academic Press Inc., N.Y.
93. Immunochemical Methods In Cell And Molecular Biology (Mayer and Walker, eds., Academic Press, London, 1987.
94. Handbook Of Experimental Immunology, Volumes I-IV, D. M. Weir and C. C. Blackwell, eds., 1986.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. An isolated nucleic acid, comprising the sequence of SEQ ID NO: 1.

2. The isolated nucleic acid of claim 1, wherein the nucleic acid encodes a polypeptide comprising the amino acid sequence of SEQ ID NO: 2.

3. A vector comprising the isolated nucleic acid of claim 2.

4. The vector of claim 3, wherein the isolated nucleic acid is operably linked to an expression cassette.

5. The vector of claim 4, wherein the expression cassette comprises a promoter selected from the group consisting of a seed-specific promoter and a constitutive promoter.

6. A transgenic plant cell comprising the vector of claim 3.

7. The transgenic plant cell of claim 6, wherein the isolated nucleic acid is operably linked to an expression cassette.

8. The transgenic plant cell of claim 7, wherein the expression cassette comprises a promoter selected from the group consisting of a seed-specific promoter and a constitutive promoter.

9. The isolated nucleic acid of claim 1, further comprising a sequence that selectively hybridizes to the sequence of SEQ ID NO: 1, wherein the nucleic acid sequence that selectively hybridizes to the sequence of SEQ ID NO: 1 is complementary to the full-length sequence of SEQ ID NO: 1.

10. An isolated polypeptide, comprising the sequence of SEQ ID NO: 2 or a sequence that is about 85% homologous to the sequence of SEQ ID NO: 2, wherein the polypeptide is a diacylglycerol acyltransferase 2 (DGAT2) polypeptide.

11. The polypeptide of claim 10, wherein the polypeptide is encoded by a nucleic acid sequence comprising the sequence of SEQ ID NO: 1.

12. The polypeptide of claim 10, wherein the polypeptide is encoded by a nucleic acid sequence that is complementary to a nucleic acid sequence that selectively hybridizes to the sequence of SEQ ID NO: 1, and wherein the nucleic acid sequence that selectively hybridizes to the sequence of SEQ ID NO: 1 is complementary to the full-length sequence of SEQ ID NO: 1.

13. A method of producing an epoxy fatty acid, comprising transforming a plant cell with a first isolated nucleic acid that encodes a diacylglycerol acyltransferase polypeptide and a second isolated nucleic acid that encodes an epoxygenase polypeptide, wherein expression of the diacylglycerol acyltransferase polypeptide and the epoxygenase polypeptide increases an amount of epoxy fatty acid in the plant cell, and wherein the first isolated nucleic acid encoding the diacylglycerol acyltransferase polypeptide is selected from the group consisting of SEQ ID NO: 1, SEQ ID NO: 4, and SEQ ID NO: 17.

14. The method of claim 13, wherein transforming the plant cell with the first isolated nucleic acid and the second isolated nucleic acid comprises transforming the plant cell with a vector comprising the first isolated nucleic acid and a vector comprising the second isolated nucleic acid.

15. The method of claim 14, wherein the first isolated nucleic acid and the second isolated nucleic acid are each operatively linked to an expression cassette.

16. The method of claim 15, wherein each expression cassette comprises a promoter selected from the group consisting of a seed-specific promoter and a constitutive promoter.

17. The method of claim 13, wherein the diacylglycerol acyltransferase polypeptide is encoded by the nucleic acid sequence of SEQ ID NO: 4.

18. The method of claim 13, wherein the diacylglycerol acyltransferase polypeptide is encoded by the nucleic acid sequence of SEQ ID NO: 17.

19. The method of claim 13, wherein the diacylglycerol acyltransferase polypeptide is encoded by the nucleic acid sequence of SEQ ID NO: 1.

20. The method of claim 13, wherein the epoxygenase polypeptide is encoded by a nucleic acid sequence comprising the sequence of SEQ ID NO: 5.

21. The method of claim 13, wherein the epoxy fatty acid is vernolic acid.

22. The method of claim 21, wherein the amount of vernolic acid in the cell is about 14 percent to about 26 percent.

23. An isolated nucleic acid, comprising the sequence of SEQ ID NO: 4.

24. A vector comprising the isolated nucleic acid of claim 23.

25. An isolated polypeptide, comprising the amino acid sequence encoded by the nucleic acid sequence of SEQ ID NO: 4.

26. An isolated nucleic acid, comprising the sequence of SEQ ID NO: 17.

27. A vector comprising the isolated nucleic acid of claim 26.

28. An isolated polypeptide, comprising the amino acid sequence encoded by the nucleic acid sequence of SEQ ID NO: 17.

* * * * *

SEQUENCE LISTING

```
<160> NUMBER OF SEQ ID NOS: 17

<210> SEQ ID NO 1
<211> LENGTH: 1017
<212> TYPE: DNA
<213> ORGANISM: Vernonia galamensis

<400> SEQUENCE: 1
atgggtgaat ttgctaatca taacagaatt aatagtaacg atgttaaaaa cgaggaaaag      60
ggcaacagcc gtgtcttcaa tggacgagaa atctatcaca ctagtatccc tcgggcatta     120
atagcattga gtttgtggat agggagtata cactttatat tgttcttgtt attcatcagt     180
tatatcttgt tcagtcctcc cacgagcgct atggttatcg gatttcaggt aattctgatg     240
gtactaccac tcgatgaaaa tagtaaattc ggcctccgaa tctttagtta tgtcagtaaa     300
tacgttatgg gacattttcc cgttaccctc tatgtagagg atatgaaatg cttccaaagc     360
aaccgagcct atgtgtttgg gttccatcct catagtgtct tcccgctggg tgttgctatc     420
ctttgcgaac acctggctgt gatcccaatt cccaatatca agttcctgac cagtaaccct     480
atcttcagaa ctcctgttct gaggcagatt tggagttggt gcggtgctat tgccgctagc     540
aaaaagaact tcacggctta tctcagcgca ggttacactt cgttgtgat tcccggtgga     600 gttcaggaga ttctccatat gagacagggt gctgagagtg ataacgtctt tatcagcagg     660
agaaagggct ttatcaaggt cgctatacag acggtaaccc cgctagtacc tgtcttcttt     720
ttcggacagg ctcatacgta caagtggtgg agacccaagt gcgaattcta cgtactgaag     780
gctagggcta ttaggttcgg acctaccgta ttctggggaa ggctcggaag ccatctgcca     840
tgtaagaatc ccacggttgt cgtagtgggt agacctatca ctgtagagaa aacgctcaag     900
cctacgatcg atgagatcag caagttccag agagagtaca cggtcagtct aaggaatctc     960
ttcgacaaat acaagacgga gatcggtcac cctggtctgg agttgaagat cttgtga      1017

<210> SEQ ID NO 2
<211> LENGTH: 338
<212> TYPE: PRT
<213> ORGANISM: Vernonia galamensis

<400> SEQUENCE: 2

Met Gly Glu Phe Ala Asn His Asn Arg Ile Asn Ser Asn Asp Val Lys
1               5                   10                  15

Asn Glu Glu Lys Gly Asn Ser Arg Val Phe Asn Gly Arg Glu Ile Tyr
            20                  25                  30

His Thr Ser Ile Pro Arg Ala Leu Ile Ala Leu Ser Leu Trp Ile Gly
        35                  40                  45

Ser Ile His Phe Ile Leu Phe Leu Leu Phe Ile Ser Tyr Ile Leu Phe
```

```
    50                  55                  60

Ser Pro Pro Thr Ser Ala Met Val Ile Gly Phe Gln Val Ile Leu Met
65                  70                  75                  80

Val Leu Pro Leu Asp Glu Asn Ser Lys Phe Gly Leu Arg Ile Phe Ser
                85                  90                  95

Tyr Val Ser Lys Tyr Val Met Gly His Phe Pro Val Thr Leu Tyr Val
            100                 105                 110

Glu Asp Met Lys Cys Phe Gln Ser Asn Arg Ala Tyr Val Phe Gly Phe
        115                 120                 125

His Pro His Ser Val Phe Pro Leu Gly Val Ala Ile Leu Cys Glu His
    130                 135                 140

Leu Ala Val Ile Pro Ile Pro Asn Ile Lys Phe Leu Thr Ser Asn Pro
145                 150                 155                 160

Ile Phe Arg Thr Pro Val Leu Arg Gln Ile Trp Ser Trp Cys Gly Ala
                165                 170                 175

Ile Ala Ala Ser Lys Lys Asn Phe Thr Ala Tyr Leu Ser Ala Gly Tyr
            180                 185                 190

Thr Cys Val Val Ile Pro Gly Gly Val Gln Glu Ile Leu His Met Arg
        195                 200                 205

Gln Gly Ala Glu Ser Asp Asn Val Phe Ile Ser Arg Arg Lys Gly Phe
    210                 215                 220

Ile Lys Val Ala Ile Gln Thr Val Thr Pro Leu Val Pro Val Phe Phe
225                 230                 235                 240

Phe Gly Gln Ala His Thr Tyr Lys Trp Trp Arg Pro Lys Cys Glu Phe
                245                 250                 255

Tyr Val Leu Lys Ala Arg Ala Ile Arg Phe Gly Pro Thr Val Phe Trp
            260                 265                 270

Gly Arg Leu Gly Ser His Leu Pro Cys Lys Asn Pro Thr Val Val Val
        275                 280                 285

Val Gly Arg Pro Ile Thr Val Glu Lys Thr Leu Lys Pro Thr Ile Asp
    290                 295                 300

Glu Ile Ser Lys Phe Gln Arg Glu Tyr Thr Val Ser Leu Arg Asn Leu
305                 310                 315                 320

Phe Asp Lys Tyr Lys Thr Glu Ile Gly His Pro Gly Leu Glu Leu Lys
                325                 330                 335

Ile Leu

<210> SEQ ID NO 3
<211> LENGTH: 1212
<212> TYPE: DNA
<213> ORGANISM: Vernonia galamensis

<400> SEQUENCE: 3
gcccatagcg agcgcgatgc attcaacagt agagacgaat accgaccatg gcagcccatc      60
catttcaagc ttttttcctt aataatgggt gaatttgcta atcataacag aattaatagt     120
aacgatgtta aaaacgagga aaagggcaac agccgtgtct tcaatggacg agaaatctat     180
cacactagta tccctcgggc attaatagca ttgagtttgt ggatagggag tatacacttt     240
atattgttct tgttattcat cagttatatc ttgttcagtc ctcccacgag cgctatggtt     300
atcggatttc aggtaattct gatggtacta ccactcgatg aaaatagtaa attcggcctc     360
cgaatcttta gttatgtcag taaatacgtt atgggacatt ttcccgttac cctctatgta     420
gaggatatga aatgcttcca aagcaaccga gcctatgtgt ttgggttcca tcctcatagt     480
gtcttcccgc tgggtgttgc tatcctttgc gaacacctgg ctgtgatccc aattcccaat     540
```

```
atcaagttcc tgaccagtaa ccctatcttc agaactcctg ttctgaggca gatttggagt    600
tggtgcggtg ctattgccgc tagcaaaaag aacttcacgg cttatctcag cgcaggttac    660
acttgcgttg tgattcccgg tggagttcag gagattctcc atatgagaca gggtgctgag    720
agtgataacg tctttatcag caggagaaag ggctttatca aggtcgctat acagacggta    780
accccgctag tacctgtctt cttttttcgga caggctcata cgtacaagtg gtggagaccc    840
aagtgcgaat tctacgtact gaaggctagg gctattaggt tcggacctac cgtattctgg    900
ggaaggctcg gaagccatct gccatgtaag aatcccacgg ttgtcgtagt gggtagacct    960
atcactgtag agaaaacgct caagcctacg atcgatgaga tcagcaagtt ccagagagag   1020
tacacggtca gtctaaggaa tctcttcgac aaatacaaga cggagatcgg tcaccctggt   1080
ctggagttga agatcttgtg aaaagacgta atcgtcttcc tgcaattgac ttcataccaa   1140
gattggacag acatcaatta cccatcataa acacaaaata aaatattaaa tataccataa   1200
caaaaaaaaa aa                                                       1212

<210> SEQ ID NO 4
<211> LENGTH: 1828
<212> TYPE: DNA
<213> ORGANISM: Vernonia galamensis

<400> SEQUENCE: 4
tctgagctca aatcaaattt ctgcgactca tacaggattc aactcaatac tttcttgatc     60
ggttctgctg ttcatttact tgtaatttct acttctgctt tgctttcatt tcaagctttt    120
ttccttaata atggcgttat tagatacgcc tcagattgga gaaataacga ccaccgccac    180
cacaactata agacggcgga ccactgtcaa gcctgatgct ggaatcggag atggattgtt    240
tgattcttcg tcgtcttcca aaaccaactc atccttcgag gatggtgaca gtttgaatgg    300
tgatttcaat gacaaattta aggaacagat cggagctggt gatgaatcca aggacgactc    360
caaggggaac ggacagaaga tagatcacgg aggagttaaa aagggacgtg aaacgactgt    420
ggtgcattat gcttatcggc cttcttctcc ggctcatcgg agaattaaag aatctccgct    480
tagctctgac gccatcttca agcagagtca tgcaggcctc tttaaccttt gcatagtggt    540
gcttgttgca gtaaatggta ggctcatcat tgagaatctg atgaagtatg gactattgat    600
caattccaac ttttggttca gttcgagatc attgagagac tggccacttc tgatgtgctg    660
cctcactcct tctgactttc cacttgctgc ctacattgtt gagaaattgg catggaaaaa    720
acgtatatcc gaccctgttg taatcacact ccatgttata ataactacaa ctgcaattct    780
ttatccggtc ttcatgattc tgaggttcga ttcagttgtt ctatcaggcg tctcgttgat    840
gctgtgtgct tgcattaatt ggttgaagtt ggtatctttt gtgcatacaa attatgacat    900
gcggtcgctt ttgaactcaa ctgataaggg agaagtggaa cccatgtctt caaatatgga    960 ttattttat gatgtcaact tcaaaagctt ggtttatttc atggttgctc aactttgtg    1020 ttaccagata agctatcctc gcactgcatt tattcgaaag ggttgggtgt acggcaact    1080 gatcaagcta gtaatattta cagggttcat ggattcatc attgaacaat atatcaatcc   1140
gattgtcaaa aattctcgtc atccattgaa aggagacttt ttatatgcga ttgagcgggt   1200
tttaaagctt tcagttccga atttatatgt gtggctctgt atgttctact gcttttttca   1260
cctttggtta aatatacttg ctgagcttct ttgttttggg gatcgtgaat tttataaga    1320 ttggtggaat gcacaaacta ttgaagagta ttggaggcta tggaatatgc ctgttcataa   1380
atggattgtt aggcaccttt atttttccatg cttgcgtaat gggataccta agggtgctgc   1440
```

```
catattggtt gcattttca tgtctgccgt gttccatgag ctttgtattg ctgttccctg    1500 ccacatttc aagttttggg cttttatcgg gatcatgttt caggtcccgt tggtcctact    1560
cacaaattac ttgcagcaca agtttcaaaa ctcgatggtg ggaaatatga tcttctggtg    1620
ctttttcagc atttttggtc aacccatgtg tgtattactt tactaccatg atgtcatgaa    1680
tcaaaagggg aaaagcaaat aaaaagatgt gattgtgttg ctccatttga tctcatagca    1740
tgactggact aaacaaaccc aagggacaca ttttagtcct aaaggaaaa ttttttgtagg    1800 aaaaaaaaaa aaaaaaaaaa aaaaaaaa                                      1828
```

<210> SEQ ID NO 5
<211> LENGTH: 1344
<212> TYPE: DNA
<213> ORGANISM: Stokesia laevis

<400> SEQUENCE: 5

```
gagaagttga ccataaatca tttatcaaca tgggtgccgg cggtcgtggt cggacatcgg     60
aaaaatcggt catggaacgt gtctcagttg atccagtaac cttctcactg agtgaattga    120
agcaagcaat ccctccccat tgcttccaga gatctgtaat ccgctcatct tactatgttg    180
ttcaagatct cattattgcc tacatcttct acttccttgc aacacatat atccctactc     240 ttcctactag tctagcctac ttagcttggc ccgtttactg gttctgtcaa gctagcgtcc    300
tcactggctt atggatcctc ggccacgaat gtggtcacca tgcctttagc aactacacat    360
ggtttgacga cactgtgggc ttcatcctcc actcatttct cctcaccccg tatttctctt    420
ggaaattcag tcaccggaat caccattcca acacaagttc gattgataac gatgaagttt    480
acattccgaa aagcaagtcc aaactcgcgc gtatctataa acttcttaac aacccacctg    540
gtcggctgtt ggttttgatt atcatgttca ccctaggatt tcctttatac ctcttgacaa    600
atatttccgg caagaaatac gacaggtttg ccaaccactt cgaccccatg agtccaattt    660
tcaaagaacg tgagcggttt caggtcttcc tttcggatct tggtcttctt gccgtgtttt    720
atggaattaa agttgctgta gcaaataaag gagctgcttg ggtagcgtgc atgtatggag    780
ttccggtatt aggcgtattt acctttttcg atgtgatcac cttcttgcac cacacccatc    840
agtcgtcgcc tcattatgat tcaactgaat ggaactggat cagaggggcc ttgtcagcaa    900
tcgataggga ctttggattc ctgaatagtg ttttccatga tgttacacac actcatgtca    960
tgcatcattt gttttcatac attccacact atcatgcaaa ggaggcaagg gatgcaatca   1020
agccaatctt gggcgacttt tatatgatcg acaggactcc aattttaaaa gcaatgtgga   1080
gagagggcag ggagtgcatg tacatcgagc ctgatagcaa gctcaaaggt gtttattggt   1140
atcataaatt gtgatcatat gcaaaatgca catgcatttt caaaccctct agttacgttt   1200
gttctatgta taataaaccg ccggtccttt ggttgactat gcctaagcca ggcgaaacag   1260
ttaaataata tcggtatgat gtgtaatgaa agtatgtggt tgtctggttt tgttgctatg   1320
aaagaaagta tgtggttgtc ggtc                                          1344
```

<210> SEQ ID NO 6
<211> LENGTH: 5
<212> TYPE: PRT
<213> ORGANISM: Vernonia galamensis

<400> SEQUENCE: 6

Leu Glu Leu Lys Ile
1               5

```
<210> SEQ ID NO 7
<211> LENGTH: 31
<212> TYPE: DNA
<213> ORGANISM: Artificial Sequence
<220> FEATURE:
<223> OTHER INFORMATION: Forward PCR primer for amplifying VgDGAT1a cDNA

<400> SEQUENCE: 7
ccaccacaac tataagacgg cggaccactg t                                      31

<210> SEQ ID NO 8
<211> LENGTH: 31
<212> TYPE: DNA
<213> ORGANISM: Artificial Sequence
<220> FEATURE:
<223> OTHER INFORMATION: Reverse PCR primer for amplifying VgDGAT1a cDNA

<400> SEQUENCE: 8
ctgaatcgaa cctcagaatc atgaagaccg g                                      31

<210> SEQ ID NO 9
<211> LENGTH: 31
<212> TYPE: DNA
<213> ORGANISM: Artificial Sequence
<220> FEATURE:
<223> OTHER INFORMATION: Forward PCR primer for amplifying VgDGAT2 cDNA

<400> SEQUENCE: 9
cgaatcttta gttatgtcag taaatacgtt a                                      31

<210> SEQ ID NO 10
<211> LENGTH: 32
<212> TYPE: DNA
<213> ORGANISM: Artificial Sequence
<220> FEATURE:
<223> OTHER INFORMATION: Reverse PCR primer for amplifying VgDGAT2 cDNA

<400> SEQUENCE: 10
taatagccct agccttcagt acgtagaatt cg                                     32

<210> SEQ ID NO 11
<211> LENGTH: 25
<212> TYPE: DNA
<213> ORGANISM: Artificial Sequence
<220> FEATURE:
<223> OTHER INFORMATION: Forward PCR primer for amplifying actin cDNA
      obtained from Vernonia galamensis

<400> SEQUENCE: 11 agggataac cacccatga atcca                                               25

<210> SEQ ID NO 12
<211> LENGTH: 25
<212> TYPE: DNA
<213> ORGANISM: Artificial Sequence
<220> FEATURE:
<223> OTHER INFORMATION: Reverse PCR primer for amplifying actin cDNA
      obtained from Vernonia galamensis

<400> SEQUENCE: 12
tgcatggtct cctgatacgg ccaag                                             25

<210> SEQ ID NO 13
<211> LENGTH: 340
<212> TYPE: PRT
<213> ORGANISM: Ricinus communis
```

```
<400> SEQUENCE: 13

Met Gly Glu Glu Ala Asn His Asn Asn Asn Asn Asn Ile Asn Ser
1               5                   10                  15

Asn Asp Glu Lys Asn Glu Glu Lys Ser Asn Tyr Thr Val Val Asn Ser
                20                  25                  30

Arg Glu Leu Tyr Pro Thr Asn Ile Phe His Ala Leu Leu Ala Leu Ser
            35                  40                  45

Ile Trp Ile Gly Ser Ile His Phe Asn Leu Phe Leu Leu Phe Ile Ser
        50                  55                  60

Tyr Leu Phe Leu Ser Phe Pro Thr Phe Leu Leu Ile Val Gly Phe Phe
65                  70                  75                  80

Val Val Leu Met Phe Ile Pro Ile Asp Glu His Ser Lys Leu Gly Arg
                85                  90                  95

Arg Leu Cys Arg Tyr Val Cys Arg His Ala Cys Ser His Phe Pro Val
            100                 105                 110

Thr Leu His Val Glu Asp Met Asn Ala Phe His Ser Asp Arg Ala Tyr
        115                 120                 125

Val Phe Gly Tyr Glu Pro His Ser Val Phe Pro Leu Gly Val Ser Val
130                 135                 140

Leu Ser Asp His Phe Ala Val Leu Pro Leu Pro Lys Met Lys Val Leu
145                 150                 155                 160

Ala Ser Asn Ala Val Phe Arg Thr Pro Val Leu Arg His Ile Trp Thr
                165                 170                 175

Trp Cys Gly Leu Thr Ser Ala Thr Lys Lys Asn Phe Thr Ala Leu Leu
            180                 185                 190

Ala Ser Gly Tyr Ser Cys Ile Val Ile Pro Gly Gly Val Gln Glu Thr
        195                 200                 205

Phe Tyr Met Lys His Gly Ser Glu Ile Ala Phe Leu Lys Ala Arg Arg
210                 215                 220

Gly Phe Val Arg Val Ala Met Glu Met Gly Lys Pro Leu Val Pro Val
225                 230                 235                 240

Phe Cys Phe Gly Gln Ser Asn Val Tyr Lys Trp Trp Lys Pro Asp Gly
                245                 250                 255

Glu Leu Phe Met Lys Ile Ala Arg Ala Ile Lys Phe Ser Pro Ile Val
            260                 265                 270

Phe Trp Gly Val Leu Gly Ser His Leu Pro Leu Gln Arg Pro Met His
        275                 280                 285

Val Val Val Gly Lys Pro Ile Glu Val Lys Gln Asn Pro Gln Pro Thr
290                 295                 300

Val Glu Glu Val Ser Glu Val Gln Gly Gln Phe Val Ala Ala Leu Lys
305                 310                 315                 320

Asp Leu Phe Glu Arg His Lys Ala Arg Val Gly Tyr Ala Asp Leu Thr
                325                 330                 335

Leu Glu Ile Leu
        340

<210> SEQ ID NO 14
<211> LENGTH: 322
<212> TYPE: PRT
<213> ORGANISM: Vernicia fordii

<400> SEQUENCE: 14

Met Gly Met Val Glu Val Lys Asn Glu Glu Val Thr Ile Phe Lys
1               5                   10                  15

Ser Gly Glu Ile Tyr Pro Thr Asn Ile Phe Gln Ser Val Leu Ala Leu
```

```
                    20                  25                  30
Ala Ile Trp Leu Gly Ser Phe His Phe Ile Phe Leu Val Ser Ser
            35                  40                  45

Ser Ile Phe Leu Pro Phe Ser Lys Phe Leu Leu Val Ile Gly Leu Leu
    50                  55                  60

Leu Phe Phe Met Val Ile Pro Ile Asn Asp Arg Ser Lys Leu Gly Gln
65                  70                  75                  80

Cys Leu Phe Ser Tyr Ile Ser Arg His Val Cys Ser Tyr Phe Pro Ile
                85                  90                  95

Thr Leu His Val Glu Asp Ile Asn Ala Phe Arg Ser Asp Arg Ala Tyr
            100                 105                 110

Val Phe Gly Tyr Glu Pro His Ser Val Phe Pro Ile Gly Val Met Ile
        115                 120                 125

Leu Ser Leu Gly Leu Ile Pro Leu Pro Asn Ile Lys Phe Leu Ala Ser
    130                 135                 140

Ser Ala Val Phe Tyr Thr Pro Phe Leu Arg His Ile Trp Ser Trp Cys
145                 150                 155                 160

Gly Leu Thr Pro Ala Thr Arg Lys Asn Phe Val Ser Leu Leu Ser Ser
                165                 170                 175

Gly Tyr Ser Cys Ile Leu Val Pro Gly Gly Val Gln Glu Thr Phe Tyr
            180                 185                 190

Met Lys Gln Asp Ser Glu Ile Ala Phe Leu Lys Ala Arg Arg Gly Phe
        195                 200                 205

Ile Arg Ile Ala Met Gln Thr Gly Thr Pro Leu Val Pro Val Phe Cys
    210                 215                 220

Phe Gly Gln Met His Thr Phe Lys Trp Trp Lys Pro Asp Gly Glu Leu
225                 230                 235                 240

Phe Met Lys Ile Ala Arg Ala Ile Lys Phe Thr Pro Thr Ile Phe Trp
                245                 250                 255

Gly Val Leu Gly Thr Pro Leu Pro Phe Lys Asn Pro Met His Val Val
            260                 265                 270

Val Gly Arg Pro Ile Glu Val Lys Gln Asn Pro Gln Pro Thr Ala Glu
        275                 280                 285

Glu Val Ala Glu Val Gln Arg Glu Phe Ile Ala Ser Leu Lys Asn Leu
    290                 295                 300

Phe Glu Arg His Lys Ala Arg Val Gly Tyr Ser Asp Leu Lys Leu Glu
305                 310                 315                 320

Ile Phe

<210> SEQ ID NO 15
<211> LENGTH: 314
<212> TYPE: PRT
<213> ORGANISM: Arabidopsis thaliana

<400> SEQUENCE: 15

Met Gly Gly Ser Arg Glu Phe Arg Ala Glu Glu His Ser Asn Gln Phe
1               5                   10                  15

His Ser Ile Ile Ala Met Ala Ile Trp Leu Gly Ala Ile His Phe Asn
            20                  25                  30

Val Ala Leu Val Leu Cys Ser Leu Ile Phe Leu Pro Pro Ser Leu Ser
        35                  40                  45

Leu Met Val Leu Gly Leu Leu Ser Leu Phe Ile Phe Ile Pro Ile Asp
    50                  55                  60

His Arg Ser Lys Tyr Gly Arg Lys Leu Ala Arg Tyr Ile Cys Lys His
65                  70                  75                  80
```

```
Ala Cys Asn Tyr Phe Pro Val Ser Leu Tyr Val Glu Asp Tyr Glu Ala
                85                  90                  95

Phe Gln Pro Asn Arg Ala Tyr Val Phe Gly Tyr Glu Pro His Ser Val
            100                 105                 110

Leu Pro Ile Gly Val Val Ala Leu Cys Asp Leu Thr Gly Phe Met Pro
        115                 120                 125

Ile Pro Asn Ile Lys Val Leu Ala Ser Ser Ala Ile Phe Tyr Thr Pro
    130                 135                 140

Phe Leu Arg His Ile Trp Thr Trp Leu Gly Leu Thr Ala Ala Ser Arg
145                 150                 155                 160

Lys Asn Phe Thr Ser Leu Leu Asp Ser Gly Tyr Ser Cys Val Leu Val
                165                 170                 175

Pro Gly Gly Val Gln Glu Thr Phe His Met Gln His Asp Ala Glu Asn
            180                 185                 190

Val Phe Leu Ser Arg Arg Gly Phe Val Arg Ile Ala Met Glu Gln
        195                 200                 205

Gly Ser Pro Leu Val Pro Val Phe Cys Phe Gly Gln Ala Arg Val Tyr
    210                 215                 220

Lys Trp Trp Lys Pro Asp Cys Asp Leu Tyr Leu Lys Leu Ser Arg Ala
225                 230                 235                 240

Ile Arg Phe Thr Pro Ile Cys Phe Trp Gly Val Phe Gly Ser Pro Leu
                245                 250                 255

Pro Cys Arg Gln Pro Met His Val Val Gly Lys Pro Ile Glu Val
            260                 265                 270

Thr Lys Thr Leu Lys Pro Thr Asp Glu Glu Ile Ala Lys Phe His Gly
        275                 280                 285

Gln Tyr Val Glu Ala Leu Arg Asp Leu Phe Glu Arg His Lys Ser Arg
    290                 295                 300

Val Gly Tyr Asp Leu Glu Leu Lys Ile Leu
305                 310

<210> SEQ ID NO 16
<211> LENGTH: 340
<212> TYPE: PRT
<213> ORGANISM: Oryza sativa

<400> SEQUENCE: 16

Met Gly Ala Asn Gly Asn Asp Val Val Ala Ala Ala Ala Gly Glu
1               5                   10                  15

Ser Pro Met Gly Ala Ala Arg Val Val Ala Glu Gly Gly Ala Thr Val
            20                  25                  30

Phe Arg Gly Ala Asp Tyr Ser Leu Pro Arg Thr Thr Val Ala Leu Ala
        35                  40                  45

Leu Trp Leu Gly Gly Ile His Phe Asn Val Phe Leu Val Leu Ala Ser
    50                  55                  60

Leu Phe Leu Phe Pro Leu Arg Val Ala Ala Met Val Val Ala Phe Gln
65                  70                  75                  80

Leu Leu Phe Met Leu Ile Pro Leu Asn Asp Lys Asp Lys Leu Gly Arg
                85                  90                  95

Lys Ile Ala Arg Phe Ile Cys Arg Tyr Ala Met Gly Tyr Phe Pro Ile
            100                 105                 110

Ser Leu His Val Glu Asp Tyr Lys Cys Phe Asp Pro Asn Arg Ala Tyr
        115                 120                 125

Val Phe Gly Phe Glu Pro His Ser Val Leu Pro Ile Gly Val Ala Ala
    130                 135                 140
```

```
Leu Ala Asp Leu Val Gly Phe Met Pro Leu Pro Lys Ile Lys Val Leu
145                 150                 155                 160

Ala Ser Ser Ala Val Phe Tyr Thr Pro Phe Leu Arg Gln Ile Trp Thr
            165                 170                 175

Trp Leu Gly Leu Ile Pro Ala Thr Arg Lys Asn Phe Gln Ser Tyr Leu
            180                 185                 190

Gly Ala Gly Tyr Ser Cys Ile Ile Val Pro Gly Gly Val Gln Glu Ile
        195                 200                 205

Leu His Met Asp His Asp Ser Glu Ile Ala Phe Leu Lys Ser Arg Lys
210                 215                 220

Gly Phe Val Lys Ile Ala Met Gln Ser Gly Cys Pro Leu Val Pro Val
225                 230                 235                 240

Phe Cys Phe Gly Gln Ser Tyr Ala Tyr Lys Trp Trp Arg Pro Lys Gly
                245                 250                 255

Lys Leu Phe Val Lys Ile Ala Arg Ala Ile Lys Phe Thr Pro Ile Val
            260                 265                 270

Phe Trp Gly Arg Tyr Gly Thr Pro Ile Pro Phe Pro Thr Pro Met His
        275                 280                 285

Val Val Val Gly Arg Pro Ile Glu Val Glu Lys Asn Ser Gln Pro Thr
290                 295                 300

Ile Asp Glu Ile Asn Glu Val His Glu Gln Phe Thr Val Ala Leu Gln
305                 310                 315                 320

Asp Leu Phe Asp Lys Tyr Lys Thr Glu Thr Gly Tyr Pro Gly Leu His
                325                 330                 335

Leu Arg Val Leu
        340
```

<210> SEQ ID NO 17
<211> LENGTH: 1738
<212> TYPE: DNA
<213> ORGANISM: Vernonia galamensis

<400> SEQUENCE: 17

```
gttcgtaatt cggctgtggt ttcctttcca acatttctac gtaatcatgg cgttgttaga      60
tacgcctcaa attggagaaa taacgacgac cgcaacaacg accattaggc agcaccccct     120
gggcaagcct gatgctggaa ttggagatgg attgttttct tcgtcgtctt ccaaaaccaa     180
ctcatccttc gaggatggtg acagtttgaa tggtgatttc aatgacaaat ttaaggaaca     240
gatcggagct ggtgatgaat ccaagaaggg gaacggaaag atagatcacg gaggagttaa     300
aaagggacgt gaaacgactg tggtgcatta tgcttatcgg ccttcttctc cggctcatcg     360
gagaattaaa gatctccgc ttagctctga cgccatcttc aagcagagtc atgcaggcct      420
ctttaacctt tgcatagtgg tgcttgttgc agtaaatggt aggctcatca tcgagaatct     480
gatgaagtat ggactattga ttaattccaa attttggttc agttcgagat cattgagaga     540
ctggccgctt ctgatgtgtt ggctgacccc ctccgacttc cccctcgccg cctacattgt     600
cgagaaattg gcatggaaaa aacgtatatc cgaccctgtt gtaatcacac tccatgttgt     660
aataactaca actgcaattc tctatccgat cttcatgatt ctgaggttcg actcggtcgt     720
tctattaggc gtctcgttga tgctgtgtgc ttgcattaat tggttgaagt tggtatcttt     780
tgtgcataca aattatgaca tgcggtcgct attgaactca actggtaagg agaagtggaa     840
gcccatgtct tcaaatatgg actactttta tgatatcaac ttcaaaagct tggtttattt     900
catggttgct ccaactttgt gttaccagat aagctatcct cgcaccgcct ttattcgaaa     960
```

```
gggctgggtg ttccggcaac tgatcaagct agtaatattt acagggttca tgggattcat    1020
cattgaacaa tatatcaatc cgattgtcaa aaattctcgg catccattga acggagactt    1080
tttatatgcg attgaacgag tattaaaggt ttcagttccg aatttatatg tgtggctctg    1140
tatgttctat tgctttttc  acctttggtt aaatatactt gctgagcttc tttggtttgg    1200
ggatcgtgaa ttttataaag attggtggaa tacacaaact attgaagagt attggaggct    1260
atggaatatg cctgttcata agtggattgt taggcacctc tattttccat gcttgcgtaa    1320
tgggatatct aagggtgctg ccatattggt tgctttttc  atgtctgccg tgttccacga    1380
gctttgcata gctgttccct gccacatttt aaagttttgg gctttcatcg ggatcatgtt    1440
ccaggtcccg ttggtactac tcacaaatta cttgcagcac aagtttcaaa actcgatggt    1500
gggaaacatg atcttttggt gcttcttcag cattttcggt caacccatgt gtgtatttct    1560
ttactaccat gaagtcaatc aaaaggggaa aagcaaatga aaggacgtta tcgtatttcc    1620
ccaatctttc ttatatcgtg aatctaatat ccataacaaa gcaaaacaat taagtcactg    1680
gagaatacta ttagcaggta ataaagaacc aaacaaaaaa aaaaaaaaaa aaaaaaaa     1738
```